United States Patent
Kim et al.

(10) Patent No.: US 10,514,790 B2
(45) Date of Patent: Dec. 24, 2019

(54) DISPLAY DEVICE AND VEHICLE HAVING THE SAME

(71) Applicant: LG ELECTRONICS INC., Seoul (KR)

(72) Inventors: Eugene Kim, Seoul (KR); Munchae Joung, Seoul (KR); Dongkuk Kim, Seoul (KR); Sunuk Kim, Seoul (KR); Hwan Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 186 days.

(21) Appl. No.: 15/504,413

(22) PCT Filed: Dec. 4, 2015

(86) PCT No.: PCT/KR2015/013187
§ 371 (c)(1),
(2) Date: Feb. 16, 2017

(87) PCT Pub. No.: WO2017/094938
PCT Pub. Date: Jun. 8, 2017

(65) Prior Publication Data
US 2017/0277323 A1    Sep. 28, 2017

(30) Foreign Application Priority Data

Dec. 1, 2015 (KR) .......................... 10-2015-0170224

(51) Int. Cl.
*G06F 3/041* (2006.01)
*G01N 21/35* (2014.01)
(Continued)

(52) U.S. Cl.
CPC ........... *G06F 3/0412* (2013.01); *G01N 21/35* (2013.01); *G06F 3/033* (2013.01); *G06F 3/044* (2013.01);
(Continued)

(58) Field of Classification Search
None
See application file for complete search history.

(56) References Cited

U.S. PATENT DOCUMENTS

2006/0158654 A1* 7/2006 Liao .................... G01P 3/366
356/445
2007/0046646 A1   3/2007 Kwon et al.
(Continued)

FOREIGN PATENT DOCUMENTS

KR   10-2012-0038318 A   4/2012
KR   10-2013-0111910 A   10/2013
(Continued)

*Primary Examiner* — Christopher R Lamb
(74) *Attorney, Agent, or Firm* — Birch, Stewart, Kolasch & Birch, LLP

(57) ABSTRACT

A display device including a touch window including an active area and an unactive area around the unactive area; a display unit disposed under the touch window; a bezel frame configured to support the display unit; and a light sensor unit disposed on a side of the bezel frame and at an angle to a top surface of the touch window under the unactive area of the touch window and including at least one light output unit configured to output light and at least one light receiving unit configured to receive light reflected from an input tool.

18 Claims, 21 Drawing Sheets

(51) Int. Cl.
*G06F 3/033* (2013.01)
*G06F 3/044* (2006.01)
*G06F 3/0488* (2013.01)
*G06F 3/042* (2006.01)

(52) U.S. Cl.
CPC .......... *G06F 3/0416* (2013.01); *G06F 3/0421* (2013.01); *G06F 3/0488* (2013.01); *G06F 2203/04101* (2013.01); *G06F 2203/04106* (2013.01)

(56) References Cited

U.S. PATENT DOCUMENTS

| | | |
|---|---|---|
| 2007/0152977 A1 | 7/2007 | Ng et al. |
| 2010/0220900 A1* | 9/2010 | Orsley .................. G06F 3/0421 382/124 |
| 2012/0045171 A1* | 2/2012 | Chen .................... G02B 6/0036 385/36 |
| 2012/0086673 A1 | 4/2012 | Chien et al. |
| 2012/0092301 A1 | 4/2012 | Park et al. |
| 2012/0092647 A1 | 4/2012 | Lim et al. |
| 2012/0113062 A1* | 5/2012 | Briden .................. G06F 3/0304 345/175 |
| 2013/0002611 A1 | 1/2013 | Kim |
| 2014/0132540 A1 | 5/2014 | Park |
| 2015/0301688 A1* | 10/2015 | Cho ...................... G06F 3/0421 345/175 |

FOREIGN PATENT DOCUMENTS

| | | |
|---|---|---|
| WO | WO 2007/103631 A2 | 9/2007 |
| WO | WO 2009/078933 A1 | 6/2009 |
| WO | WO 2011/083956 A2 | 7/2011 |

\* cited by examiner

FIG.1
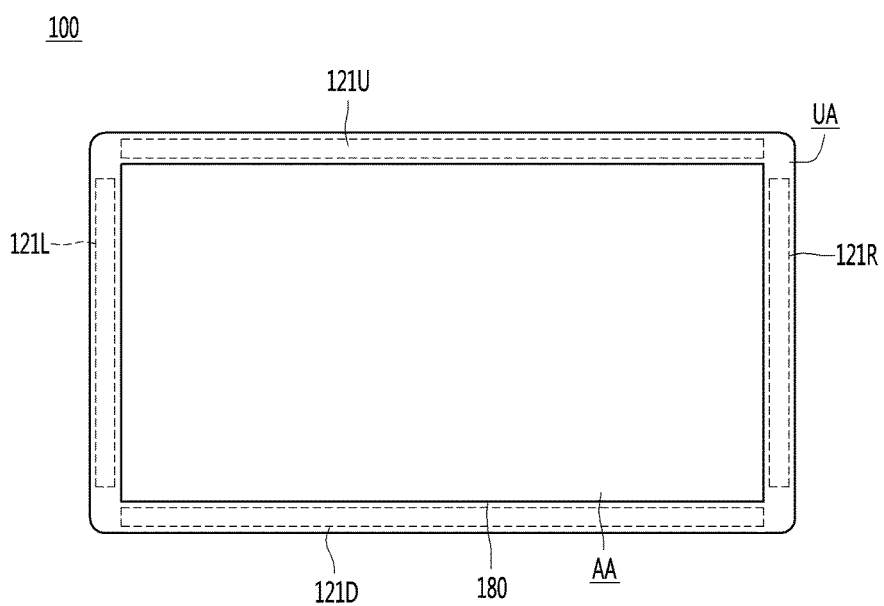
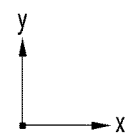

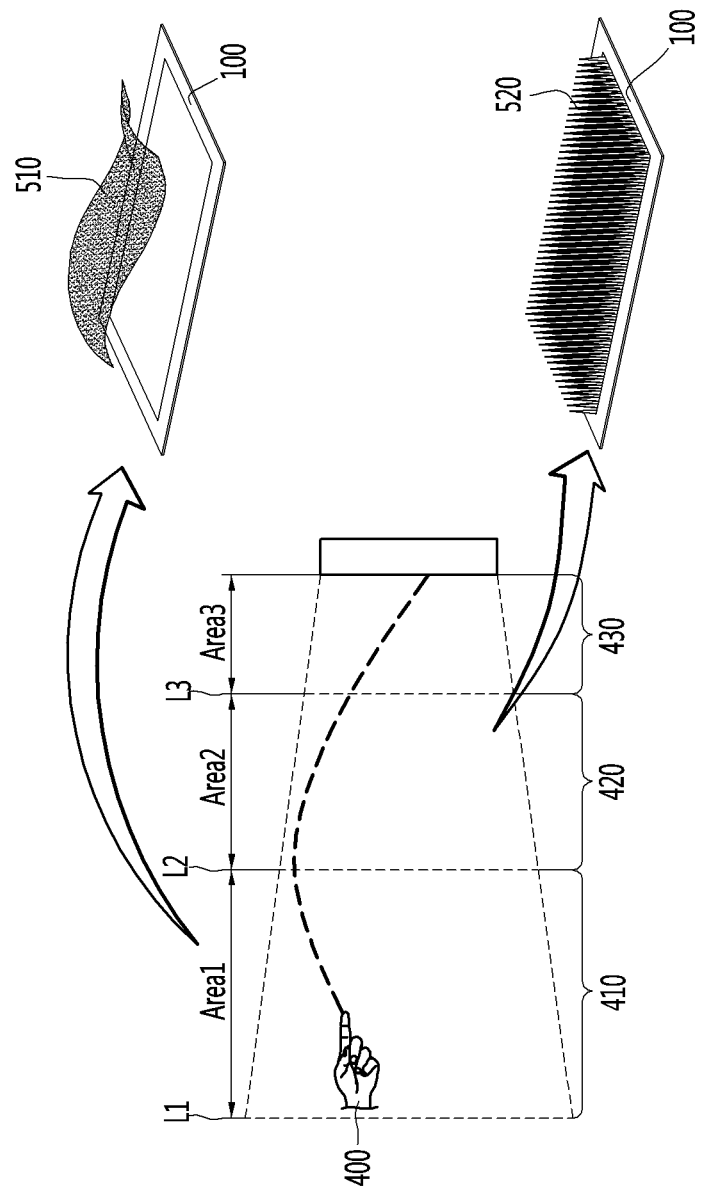

DISPLAY DEVICE AND VEHICLE HAVING THE SAME

CROSS REFERENCE TO THE RELATED APPLICATIONS

This application is the National Phase of PCT International Application No. PCT/KR2015/013187, filed on Dec. 4, 2015, which claims priority under 35 U.S.C. 119(a) to Patent Application No. 10-2015-0170224, filed in Korea on Dec. 1, 2015, all of which are hereby expressly incorporated by reference into the present application.

BACKGROUND OF THE INVENTION

Field of the Invention

The present disclosure relates to a display device and a vehicle having the same.

Description of the Related Art

In general, a display device regulates the light transmittance of liquid crystal cells arranged in the form of a matrix to display a desired image, and uses light irradiated to a backlight unit to form an image on a liquid crystal panel. Due to characteristics, such as light weight, thin thickness and low power consumption, a gradual increase in application range of a liquid crystal display (LCD) using such a principle is a modern trend. In addition, according to such a trend, the LCD is being used for office automation equipment, audio/video equipment or the like.

The LCD is also being widely applied to a display device for a vehicle navigation system, and a portable display device for a notebook computer, a mobile phone, or the like, as well as to a computer monitor or TV. Such a display device can be combined with a touch panel to provide an image to be displayed on a display and a touch interface through a touch input.

Furthermore, due to development in touch technology and 3D technology, a research on a technology that allows 3D interaction is active. The 3D interaction is a technology that includes sensing a Z axis input as well as X-Y axis input sensing at a typical touch sensor. Efforts to implement a proximity touch or space recognition are also being made for 3D interaction implementation. For example, technologies that sense the Z axis input by using a camera based or ultrasound based general sensor module.

However, the above-described sensors have a limitation in that a success rate of proximity space recognition is low due to resolution or a viewing angle. Also, since there is a need to provide a separate space for disposing sensors with the displace device, there are limitations in that the size of the display device increases and there is a constraint on design.

SUMMARY OF THE INVENTION

An object of the present invention is to provide a display device that enhances user convenience and has a decreased size, and a vehicle having the same.

In one embodiment, a display device includes a touch window on which an active area and an unactive area around the unactive area are defined; a display unit disposed under the touch window; a bezel frame configured to support the display unit; and a light sensor unit disposed under the unactive area of the touch window and including at least one light output unit that outputs light and at least one light receiving unit that receives light reflected from a user input tool, wherein the light sensor unit is disposed at an angle to a top surface of the touch window. Another embodiment provides a vehicle including the above-described display device.

A display device according to an embodiment includes a light sensor unit and a touch sensor unit to continuously track a proximity touch, a floating touch, and a direct touch according to a distance to an input tool and sense them at high resolution.

In addition, a light sensor unit of a display device according to an embodiment has a structure in which it is effectively integrated with a bezel frame including a display unit and with a front case, thus it is possible to decrease the size of bezel and enhance sensibility. In particular, a light sensor unit can be disposed so that a light sensor substrate inclines, and thus enables light to be evenly transmitted onto an active area. Also, a lens of a light sensor unit includes a concave surface and thus enables light to be evenly transmitted onto an active area.

Thus, since the numbers of light output units and light receiving units decrease in addition to resolution enhancement and it is possible to dispose a light sensor unit only on a portion of an unactive area there are advantages in that it is possible to reduce manufacturing costs and decrease the size of bezel. As another example, since a light sensor substrate is disposed at an angle and a lens includes a concave surface, the light sensor unit can enable light to be evenly transmitted onto an active area.

Also, it is possible to dispose a light sensor unit at a bezel frame to further decrease the size of bezel and stably support a light sensor unit. Thus, since the numbers of light output units and light receiving units may decrease in addition to resolution enhancement and it is possible to dispose a light sensor unit only on a portion of an unactive area, there are advantages in that it is possible to reduce manufacturing costs and decrease the size of bezel.

In addition, the above-described display device is a breadthwise display device and has a shape suitable for a vehicle. In addition, since the light sensor unit of the breadthwise display device is disposed in a structure resistant to vibration, it is possible to precisely sense a proximity touch even in a shaking vehicle. Also, by selecting or highlighting a menu displayed on a display or a specific item in the menu according to a distance to a user's hand, it is possible to easily select the menu or the specific item in the menu within a vehicle that vibrates.

Further scope of applicability of the present invention will become apparent from the detailed description given hereinafter. However, the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by illustration only, and thus are not limitative of the present invention, and wherein:

FIG. 1 is a top view of a display device according to an embodiment.

FIG. 7 is a diagram illustrating the operations of a light output unit and a touch sensor unit in FIG. 5.

DETAILED DESCRIPTION OF EMBODIMENTS OF THE INVENTION

Figure 2:
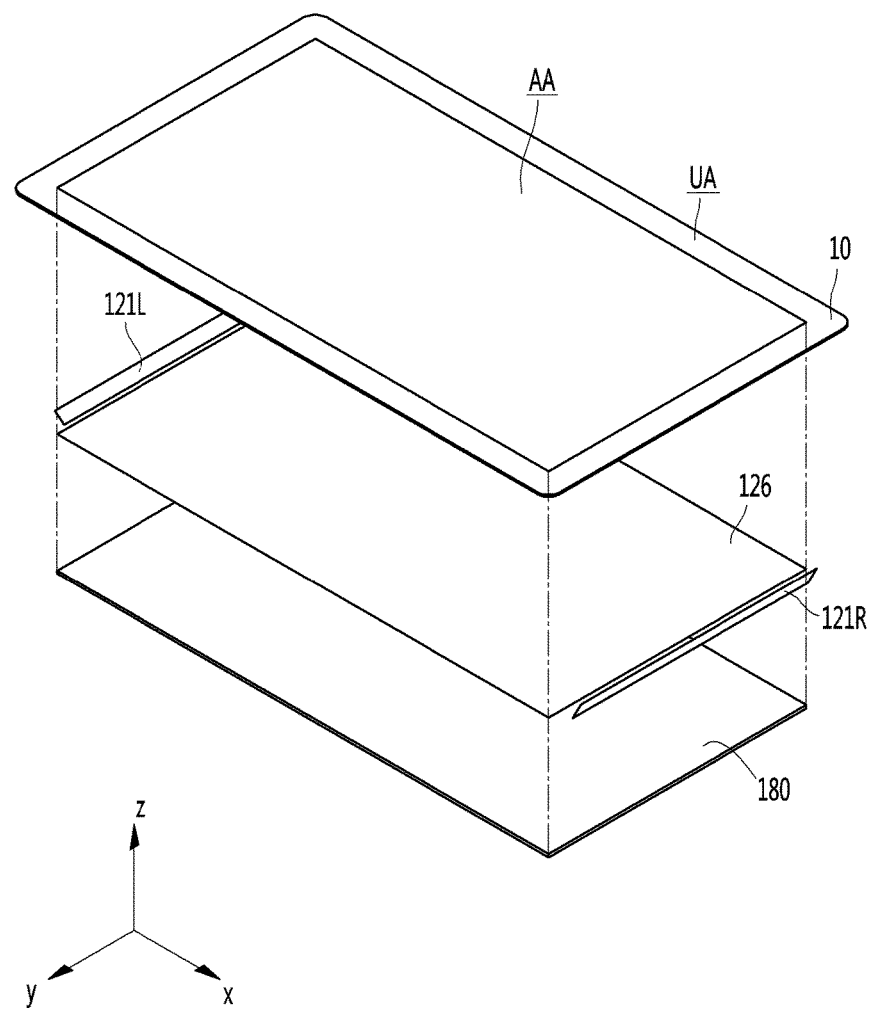
FIG. 2 is a schematic exploded perspective view of a display device according to an embodiment.

Hereinafter, embodiments are described in detail with reference to the accompanying drawings and regardless of the numbers of the drawings, same or similar components are assigned with the same reference numerals and thus repetitive descriptions for those are omitted. Since the suffixes "module" and "unit" for components used in the following description are given and interchanged for easiness in making the present disclosure, they do not have distinct meanings or functions. In describing the embodiments disclosed in the present disclosure, detailed descriptions of related known technologies will be omitted because they would obscure the subject of the embodiments disclosed in the present disclosure. Also, the accompanying drawings are used to help easily understanding embodiments disclosed herein but the technical idea disclosed in the present disclosure is not limited thereto. It should be understood that all of variations, equivalents or substitutes contained in the concept and technical scope of the inventive concept are also included.

Although the terms 'first' and 'second' may be used to describe various components, these components should not be limited to these terms. The terms are used only in order to distinguish a component from another component. When it is mentioned that any component is "connected" or "accessed" to another component, it should be understood that the former can be directly connected to the latter, or there may be another component in between. On the contrary, when any component is referred to as being 'directly connected' or 'directly accessed' to another component, it should be understood that there may be no other component in between.

The terms in singular form include the plural form unless otherwise specified. The term "includes" or "has" indicates the presence of characteristics, numbers, steps, operations, components, parts or combinations thereof represented in the present disclosure but does not exclude the presence or addition of one or more other characteristics, numbers, steps, operations, components, parts or combinations thereof.

When it is described that an element or layer is "on" another element or layer, the element or layer may be directly on the other element or layer or an intermediate element or layer may be in between. On the contrary, when it is described that the element or layer is "directly on" the other element or layer, there is no intermediate element or layer in between.

The spatially relative terms "below", "beneath", "lower", "above" and "upper" may be used to easily describe the correlation between an element or component and another element or component as shown in the drawings. The spatially relative terms should be understood as terms including different directions of an element in use or in operation in addition to the direction shown in the drawings. For example, when turning the element shown in the drawings upside down, the element "below" or "beneath" the other element can be disposed above the other element. Thus, the term "below" or "beneath" may include both lower and upper directions.

A vehicle discussed in the present disclosure may include a car or motorcycle. In the following, the car of the vehicle is mostly discussed. The vehicle discussed in the present disclosure may include all of an internal combustion engine vehicle that includes an engine as a power source, a hybrid vehicle that includes an engine and an electrical motor as a power source, and an electrical vehicle that includes an electrical motor as a power source.

In the following description, the right side of the vehicle means the left side of the driving direction of the vehicle and the right side of the vehicle means the right side of the driving direction of the vehicle. A left hand drive (LHD) vehicle is mostly described unless mentioned to the contrary.

A display device according to an embodiment may be a display device allowing 3D interaction, include a light sensor unit and perform a proximity touch and space recognition. In particular, when a user's hand gradually approaches the front surface of the display device, the light sensor unit of the display device can recognize all routes, sections and positions of the hand until a touch input is performed (hand detection), and when the distance to the hand is within a third distance L3 (in FIG. 6A), the light sensor unit can recognize a finger (finger detection). Thus, it is possible to solve a problem with a decrease in a success rate of proximity space recognition due to a resolution or a viewing angle.

That is, the display device can sense the spatial position of a user's hand through the light sensor unit and sense a floating touch or a direct tough through a touch sensor unit. Next, the display device according to an embodiment is described in detail with reference to FIGS. 1 and 2.

As shown, the display device 100 according to an embodiment may include a touch window 10, a touch sensor unit 126, a display unit 180, and a light sensor units 121L, 121R, 121U or 121D. In the following, when mentioning any one of the light sensor units 121L, 121R, 121U or 121D, a reference number 121 is provided.

In a top view as shown in FIG. 1, the display device 100 according to an embodiment can be defined by an active area AA and an unactive area UA. For example, the active area AA may be a rectangle shape in which the horizontal direction (x direction) is longer. In addition, the unactive area UA can be disposed to surround the edges of the active area AA. That is, the display device 100 according to the embodiment can be a breadthwise display device in which the horizontal direction is longer, and such a breadthwise display is suitable for a vehicle display that displays various functions and performs route guidance.

In addition, a display can be displayed on the active area AA and the display not displayed on the unactive area UA. That is, the active area AA and the unactive area UA can be divided by the presence and absence of the display. Also, it is possible to sense the position (e.g., direct touch) of an input tool (e.g., finger) on at least one of the active area AA and the unactive area UA. That is, the active area AA and the unactive area UA can be divided according to whether it is possible to sense a touch input.

Further, it is possible to sense the spatial position (e.g., 3D interaction) of an input tool (e.g., finger) on at least one of the active area AA and the unactive area UA. That is, the active area AA and the unactive area UA can be divided according to whether it is possible to sense a proximity touch.

For proximity touch sensing, the light sensor unit 121 may include a light output unit that outputs light and a light receiving unit that receives the scattered and/or reflected light of the output light. Specifically, the light output unit can output light onto the active area AA (z axis), and the light receiving unit can receive the light reflected from the input tool on the active area AA and sense the spatial position of the input tool.

Such a light sensor unit 121 can be disposed at least one side of the unactive area UA. In the top view shown in FIG. 1, such a light sensor unit 121 includes the first light sensor unit 121L disposed at the left side (−x axis direction) of the active area AA. Also, the light sensor unit 121 includes the second light sensor unit 121R disposed at the right side (x axis direction) of the active area AA, the third light sensor unit 121U disposed on the active area AA (y axis direction), and the fourth light sensor unit 121D disposed under the active area AA (−y axis direction).

In an embodiment, the breadthwise display device 100 may include only some of the first to fourth light sensor units 121L, 121R, 121U, and 121D to decrease the size of the unactive area UA and decrease the size of bezel of the display device 100. Specifically, in one embodiment in FIG. 2, the breadthwise display device 100 includes the first light sensor unit 121L and the second light sensor unit 121R that are disposed at breadthwise sides of the active area AA.

That is, the first light sensor unit 121L can sense the position of the input tool on the left active area AA, and the second light sensor unit 121R can sense the position of the input tool on the right active area AA to sense the position of a hand at high precision and decrease the size of bezel.

In another embodiment, the breadthwise display device 100 may include the third light sensor unit 121U and the fourth light sensor unit 121D that are disposed at short sides of the active area AA. That is, the third light sensor unit 121U or the fourth light sensor unit 121d that are disposed in a breadthwise direction may cover a whole of the short active area AA to decrease the unactive area UA occupied by the light sensor unit 121 and decrease the size of bezel.

In the following, the display device 100 according to an embodiment is described to include the first light sensor unit 121L and the second light sensor unit 121R, and the descriptions of the first light sensor unit 121L and the second light sensor unit 121R may be applied to all the light sensor units 121 that are disposed at various positions.

Further, the light sensor unit 121 that is partially disposed as described above preferably outputs light to be capable of covering a whole of the front surface of the active area AA and receive reflected light so that precision in the space recognition of an input tool may be enhanced.

In the following, the structure of the display device in which the light sensor unit 121 effectively covers the front surface of the active area AA is described. Referring to FIG. 2, such a display device 100 includes a touch window 10, a touch sensor unit 126 under the touch window 10, a light sensor unit 121 under the touch window 10, and a display unit 180 under the touch sensor unit 126.

In addition, the touch window 10 can have a size that covers both the active area AA and the unactive area UA. In addition, the touch sensor unit 126 and the display unit 180 can be disposed under the active area AA of the touch window 10.

Specifically, detection electrodes that sense a touch on the touch sensor unit 126 can have a size corresponding to the active area AA and be disposed under the touch window 10. In addition, an area of the display unit 180 which displays an image can have a size corresponding to the active area AA and be disposed under the touch sensor unit 126. However, the embodiment is not limited thereto and the touch sensor unit 126 and the display unit 180 may be integrally formed in the embodiment.

In addition, the light sensor unit 121 can be disposed on a side of the touch sensor unit 126 and/or the display unit 180. That is, the light sensor unit 126 can be disposed in the space of the unactive area UA that the touch sensor unit 126 and the display unit 180 do not occupy. In addition, the light sensor unit 121 can be disposed under the unactive area UA of the touch window 10. Specifically, the first light sensor unit 121L and the second light sensor unit 121R can be disposed under left and right unactive areas UA, respectively.

If the light sensor unit 121 is disposed on the active area AA in the vertical direction (z axis direction), there are limitations in that precision in space recognition decreases because it is possible to output light to the top surface of the active area AA (a direction including x axis and y axis) but it is difficult to output light in a vertical direction, and the unactive area UA of the display device 100 protrudes.

Under the unactive area UA of the touch window 10, such a light sensor unit 121 may output light toward the touch window 10 and receive reflected light. In the following, optical properties are described based on light output but the optical properties may also be equally applied to light reception.

When the light sensor unit 121 outputs light in a direction perpendicular to the top surface of the touch window 10 (z axis direction), only light laterally spread among output light may enter the active area AA. Thus, it may be difficult to cover the front surface of the breadthwise display device 100 with output light.

Thus, the light sensor unit 121 can be disposed at an angle to the touch window 10 so that it is possible to output light toward the active area AA. Specifically, the top surface of the light sensor unit 121 can have a slope with respect to the top surface of the touch window 10. More specifically, the top surface of the light sensor unit 121 can be disposed at an angle to face the active area AA of the touch window 10.

Since such a light sensor unit 121 is disposed at an angle, a laterally occupied area decreases and a majority of output light is output toward the active area AA, and thus it is possible to output light to effectively cover the breadthwise active area AA. For example, light that the light sensor unit 121 outputs is emitted toward the active area AA, and thus light can be transmitted at an angle of 10 degrees to 35 degrees to the top surface of the touch window 10. That is, since the light that the light sensor unit 121 outputs has a narrow angle to the top surface of the touch window 10, it is possible to sufficiently cover the active area AA.

In summary, since the light sensor unit 121 is disposed only at a portion of the unactive area UA of the breadthwise display device 100, it is possible to decrease the size of bezel. Since the light sensor unit is disposed under the unactive area UA, it is possible to prevent the unactive area UA from protruding and at the same time, and it is possible to output sufficient light in a vertical direction. Since the light sensor unit is disposed at an angle, it is possible to cover the front surface of the active area AA and at the same time, it is possible to decrease the size.

Figure 3A:
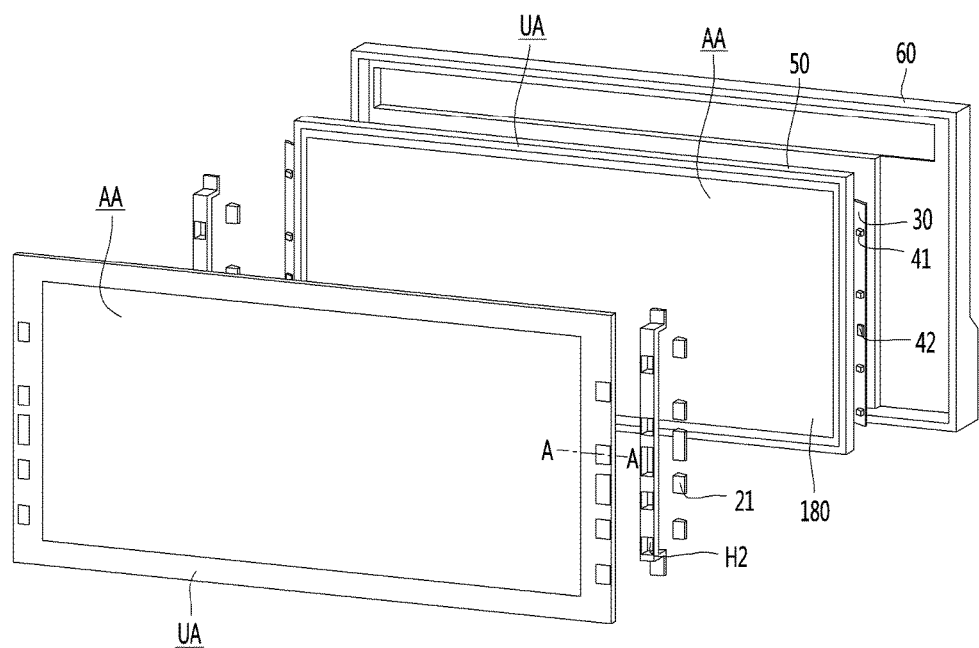
FIGS. 3A to 3D are diagrams illustrating a particular example of the display device of FIG. 1.
Figure 3B:
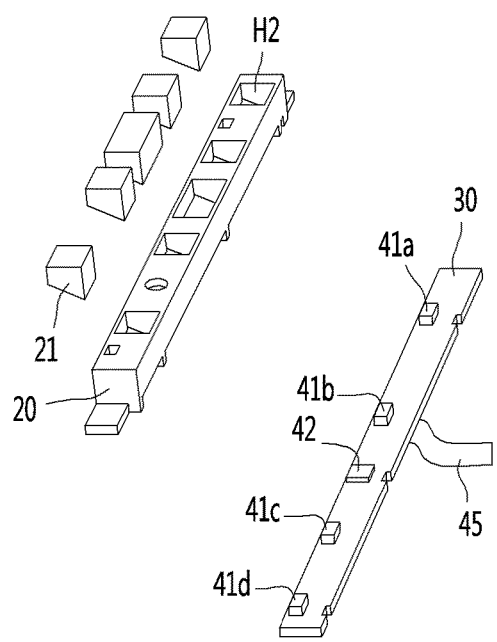
Figure 3C:
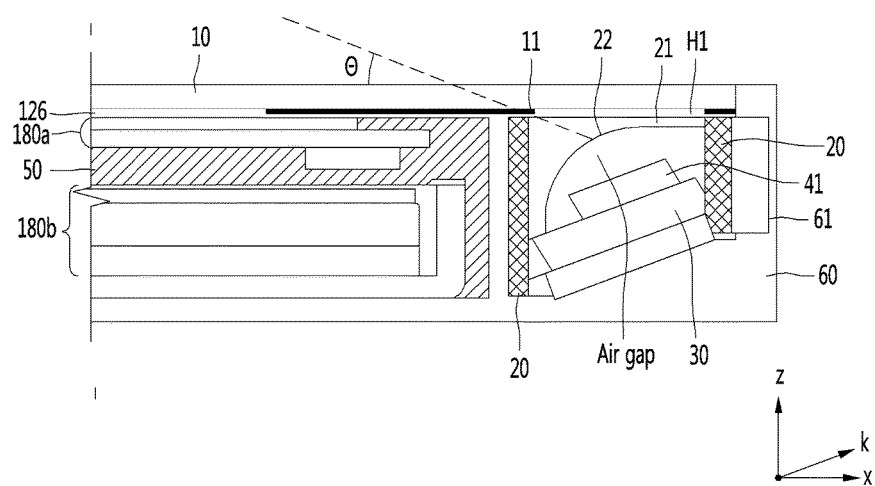
Figure 3D:
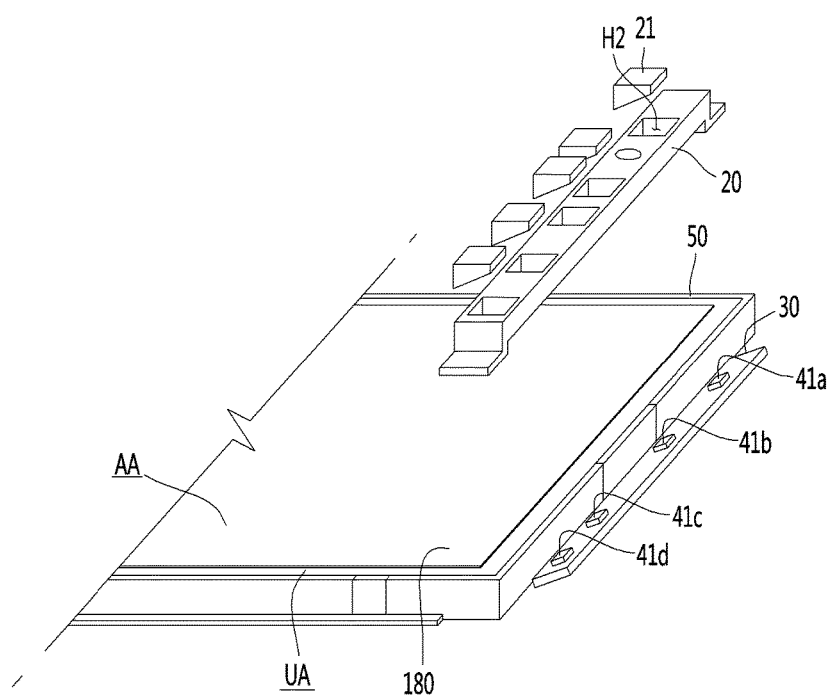

In the following, a particular example of the display device 100 is described with reference to FIGS. 3A to 3D. In particular, FIG. 3A is an exploded perspective view of the display device 100, FIG. 3B is an exploded perspective view of the light sensor unit 121, FIG. 3C is a cross-sectional view of line A-A' in FIG. 3A, and FIG. 3D is a detailed perspective view of the light sensor unit 121 in the display device 100.

Referring to FIGS. 3A to 3D, the display device 100 includes the touch window 10, the touch sensor unit 126 disposed under the touch window 10, the display unit 180 disposed under the touch sensor unit 126, a bezel frame 50 that supports the display unit 180, the light sensor unit 121 disposed under the touch window 10, and a front casing 60 that supports them.

Specifically, the active area AA of the touch window 10 may be transparent in order to show an image displayed on the display unit 180. Such a touch window 10 may include glass or plastic. Specifically, the touch window 10 may include chemical strengthening/heat strengthening glass, such as aluminosilicate glass or soda lime glass. Alternatively, the touch window 10 may include reinforced or flexible plastic, such as polyimide (PI), polyethylene terephthalate (PET), propylene glycol (PPG), or poly carbonate (PC), or sapphire.

Also, the touch window 10 may include an optically isotropic film. As an example, the touch window 10 may include cyclic olefin copolymer (COC), cyclic olefin polymer (COP), optically isotropic polycarbonate (PC), optically isotropic PMMA, or the like. In addition, the unactive area UA of the touch window 10 may be opaque in order not to show various components that are disposed thereunder. Thus, an opaque printed layer 11 can be disposed on the unactive area UA of the touch window 10.

However, the printed layer 11 may not be disposed on at least a portion of the unactive area UA. Specifically, the printed layer 11 may include a first hole H1. Such a first hole H1 can be disposed at a position corresponding to the light output unit 41 and the light receiving unit 42 of the light sensor unit 121. That is, the first hole H1 of the printed layer 11 can be disposed to overlap the light output unit 41 and the light receiving unit 42.

Such a printed layer 11 may be formed by the applying of a material having a certain color so that a wiring disposed on the unactive area UA and a printed circuit board connecting the wiring to an external circuit do not show when seen from the outside. That is, the printed layer 11 can have a color suitable for a desired appearance and include e.g., black or white pigment to represent black or white. Alternatively, it is possible to use various color films to represent various colors, such as red or blue.

The touch sensor unit 126 can be disposed under such a touch window 10. The touch sensor unit 126 may include an electrode. In addition, if an input device is in contact with the display device 100, capacitance that appears between a part being in contact with the input device and the electrode is detected and thus the display device 100 can sense the part having such a difference as a contact position.

Here, the electrode may include a transparent conductive material so that electricity may flow without interruption of light transmission. As an example, the electrode may include at least one of ① metal oxide, such as indium tin oxide or indium zinc oxide; ② nano wire, photosensitive nano wire film, CNT, graphene, conductive polymer, or a mixture thereof; ③ Cr, Ni, Cu, Al, Ag, Mo, Au, Ti and an alloy thereof.

Such a touch sensor unit 126 may include the active area AA, and the active area AA of the touch sensor unit 126 can be disposed to overlap the active area AA of the touch window 10 to sense the direct touch and/or floating touch of an input tool. For example, the electrode that senses a touch on the touch sensor unit 126 can be disposed on the active area AA.

In addition, the touch sensor unit 126 may include the unactive area UA, and the unactive area UA of the touch sensor unit 126 may be smaller than the size of the unactive area UA of the touch window 10. Thus, an empty space may be formed on a side of the unactive area UA of the touch sensor unit 126.

The display unit 180 can be disposed under the touch sensor unit 126. However, an in-cell structure in which the touch sensor unit 126 is disposed in the display unit 180 may be also possible. The display unit 180 may correspond to at least one of a liquid crystal display (LCD), a thin film transistor-liquid crystal display (TFT LCD), an organic light-emitting diode (OLED), a flexible display, a 3D display, and an e-ink display.

In an embodiment, the display unit 180 may be the TFT LCD and include a liquid crystal panel 180*a* and a backlight unit 180*b*. Specifically, the liquid crystal panel 180*a* may include a color filter array substrate, a TFT array substrate, and a liquid crystal layer that is in between, and polarization plates may be attached to the external surfaces of the color filter array substrate and the TFT array substrate, respectively.

In addition, the crystal liquid panel 180*a* is formed so liquid crystal cells forming a pixel unit are arranged in the form of a matrix, and the liquid crystal cells regulate light transmittance according to image signal information received from a driver actuating circuit to form an image. The backlight unit 180*b* that supplies light can be disposed under the liquid crystal panel 180*a* so that the difference in transmittance that the liquid crystal panel 180*a* represents is externally expressed.

The backlight unit 180*b* may include an LED assembly that is arranged in the length direction of at least edge of a support main, a white or silver reflector, a light guide plate that is placed on the reflector, and an optical sheet that is placed thereon. Light emitted from a plurality of LEDs may be provided to the liquid crystal panel 180*a* via the light guide plate and pass through the liquid crystal panel 180*a*, thus the display unit 180 may display an image.

Such a display unit 180 may include the active area AA and the unactive area UA. Specifically, the active area AA of the display unit 180 is an area that displays an image, and have a size corresponding to the active area AA of the touch window 10. In addition, the unactive area UA of the display unit 180 is an area on which a wiring electrode is disposed, and may be smaller than the unactive area UA of the touch window 10. Thus, an empty space may be formed on a side of the unactive area UA of the touch sensor unit 126.

The bezel frame 50 that supports the liquid crystal panel 180*a* and the backlight unit 180*b* may be further disposed. For example, the bezel frame 50 may include a first receiving portion disposed at an upper part, and the first receiving portion may hold the liquid crystal panel. Also, the bezel frame may include a second receiving portion disposed therein, and the backlight unit 180*b* may be mounted on the second receiving portion.

Such a bezel frame 50 may be larger than the active area AA of the touch window 10 and smaller than the unactive area UA. In addition, the light sensor unit 121 can be disposed in the empty space on a side of the bezel frame 50. That is, the light sensor unit 121 can be disposed under the unactive area UA of the touch window 10 and on the side of the bezel frame 50.

Referring to FIG. 3B, such a light sensor unit 121 may include a noise reducing frame 20, the light output unit 41, the light receiving unit 42, a lens 21, and a light sensor substrate 30. The light output unit 41 may output e.g., infrared (IR) light in order to sense an input tool that is placed on the active area AA (z axis). Specifically, the light output unit 41 may be a photo diode that outputs light in an infrared wavelength band.

Also, the light receiving unit 42 receives scattered or reflected light when the light output from the light output unit 41 is reflected from the input tool on the top surface of the active area AA. In particular, the light receiving unit 42 may include a photo diode and convert received light into an electrical signal through the photo diode. The electrical signal obtained through the conversion may be input to a processor 170 (see FIG. 5).

The noise reducing frame 20 enhances the linearity of light output from the light output unit 41 to guide the light upwards, collects the light reflected from the input tool, and blocks noise, such as light emitted from the display unit 180. Such a noise reducing frame 20 can be disposed under the unactive area UA of the touch window 10. Also, the noise reducing frame 20 can be disposed on a side of the bezel frame 50.

In addition, the noise reducing frame 20 can have a second hole H2 for light transmission, and such a second hole H2 may correspond to the first hole H1 of the printed layer 11. In addition, the lens 21 can be disposed in the second hole H2 of the noise reducing frame 20. That is, the lens 21 can be inserted in the second hole to cover the second hole H2.

Such a lens 21 may be transparent and thus transmit light (e.g., infrared light). That is, the lens 21 may include glass and/or plastic. Specifically, the lens 21 disposed on the light output unit 41 can transmit the light emitted from the light output unit 41 onto the active area AA. Also, the lens 21 disposed on the light receiving unit 42 may guide the light reflected from the input tool to the light receiving unit 42.

In particular, the lens 21 changes the route of light from the light output unit 41 toward the active area AA in order to guide reflected light to the light receiving unit 42. Specifically, the lens 21 may include a concave surface. For example, the internal surface 22 of the lens 21 may be formed in a concave shape to enable the light output from the light output unit 41 to be emitted so that the light is further spread toward the active area AA. Likewise, the concave surface 22 enables the light reflected from the input tool to be collected by the light receiving unit 42 through the lens 21 to enhance the precision in proximity sensing and decreasing the size of the light sensor unit 121.

Turning back to the description of the noise reducing frame 20, the noise reducing frame 20 may be in a bar shape. Specifically, the noise reducing frame 20 is in a square pillar shape that is extended along the unactive area UA, and at least one side thereof may be open. In addition, the light sensor substrate 30 is inserted in the open area of the noise reducing frame 20 so that an internal space surrounded by the light sensor substrate 30 and the noise reducing frame 20 may be formed. In addition, the light output unit 41 and the light receiving unit 42 can be disposed on the light sensor substrate in the internal space.

That is, referring to FIG. 3D, the light sensor substrate 30 may be coupled to the lower end of a side of the bezel frame 50, the noise reducing frame 20 can be disposed to cover the light sensor substrate 30, and the lens 21 can be disposed in the second hole H2 of the noise reducing frame 20. Thus, the light output unit 41 and the light receiving unit 42 can be surrounded by the noise reducing frame 20, the light sensor substrate 30, and the lens 21.

As such, at least one light output unit 41 and at least one light receiving unit 42 can be disposed on the light sensor substrate 30, and a light sensor wiring 45 (FIG. 3B) that supplies power to the light output unit 41 and to the receiving unit 42 and transmits information sensed from the light receiving unit 42 may be connected thereto.

For example, along the length of the light sensor substrate 30, the first light output unit 41*a*, the second light output unit 41*b*, the light receiving unit 42, the third light output unit 41*c*, and the fourth light output unit 41*d* can be disposed at intervals. The number of the light output units 41 may be larger than that of the light receiving units 42. The reason is to evenly output light from the display device 100.

In addition, the positions of the first light output unit 41*a*, the second light output unit 41*b*, the light receiving unit 42, the third light output unit 41*c*, and the fourth light output unit 41*d* may overlap the position of the lens 21, as described earlier. Air gaps may also be formed between the lens 21 and the light output unit 41 and between the lens 21 and the light receiving unit 42. In this instance, the air gap between the light output unit 41 and the lens may be larger than that between the light receiving unit 42 and the lens 21. Thus, the light output unit 41 outputs light more efficiently and the light receiving unit 42 can perform light reception more efficiently.

Further, referring to FIG. 3C, the light sensor substrate 30 can be disposed at an angle. Specifically, the light sensor substrate 30 can be disposed at an angle to the touch window 10. More specifically, the top surface of the light sensor substrate 30 can have a slope with respect to the top surface of the touch window 10. For example, when the top surface of the active area AA is defined as a horizontal plane, the top surface of the light sensor substrate 30 may be at an angle to the horizontal plane. In a side view, a first end of the light sensor substrate 30 in the length direction can be disposed at a higher position than a second end in the length direction.

In this instance, the tilt direction (k axis) of the light sensor substrate 30 may be a direction that enables the top surface of the light sensor substrate 30 to face the active area AA. Thus, the light output from the light output unit 41 disposed on the top surface of the light sensor substrate 30 may be output toward the active area AA. Furthermore, the light output toward the active area AA can be emitted through the concave surface 22 of the lens 21 to be further bent toward the active area AA. Thus, since output light may evenly cover the active area AA, the number of the light output units 41 may decrease.

Since a similar optical property may also be applied to the light reflected from the input tool, the light receiving unit 42 may effectively collect reflected light. For example, light that the light sensor unit 121 outputs is emitted toward the active area AA, thus can be transmitted at an angle θ of 10 degrees to 35 degrees to the top surface of the touch window 10. That is, since the light that the light sensor unit 121 outputs has a narrow angle to the top surface of the touch window 10, it is possible to sufficiently cover the active area AA.

Further, the front casing 60 supports the touch window 10, the bezel frame 50, and the light sensor unit 121 as described earlier. Specifically, the touch window 10 can be disposed on the front casing 60 to form an internal space, and the bezel frame 50 and the light sensor unit 121 can be disposed in the internal space.

Such a front casing 60 may further include a bumper portion 61 adjacent to the noise reducing frame 20. The bumper portion 61 may cancel vibration transmitted from the front casing 60 so that the light sensor unit 121 is fixed. Further, when the display device 100 is installed in the vehicle, vibration transmitted from the vehicle may occur, in which case the buffer portion 61 may cancel such vibration to enhance precision in proximity touch by the light sensor unit 121.

In addition, the front casing 60 may support the light sensor substrate 30, a surface thereof that supports the light sensor substrate 30 may be formed as a slope corresponding to the light sensor substrate 30, but the embodiment is not limited thereto. Since the light sensor substrate 30 is disposed at an angle and the lens 21 includes the concave surface 22, the light sensor unit 121 according to such a particular embodiment may enable light to be evenly transmitted onto the active area AA.

Thus, since the numbers of light output units 41 and the light receiving units 42 may decrease in addition to resolution enhancement and it is possible to dispose the light sensor unit 121 only on a portion of the unactive area UA, it is possible to reduce manufacturing costs and decrease the size of bezel.

Another particular example of the display device 100 will now be described with reference to FIGS. 4A to 4C. In this instance, descriptions equal to the previously provided example may be omitted, and the same reference numerals are assigned to components having the same function.

Figure 4A:
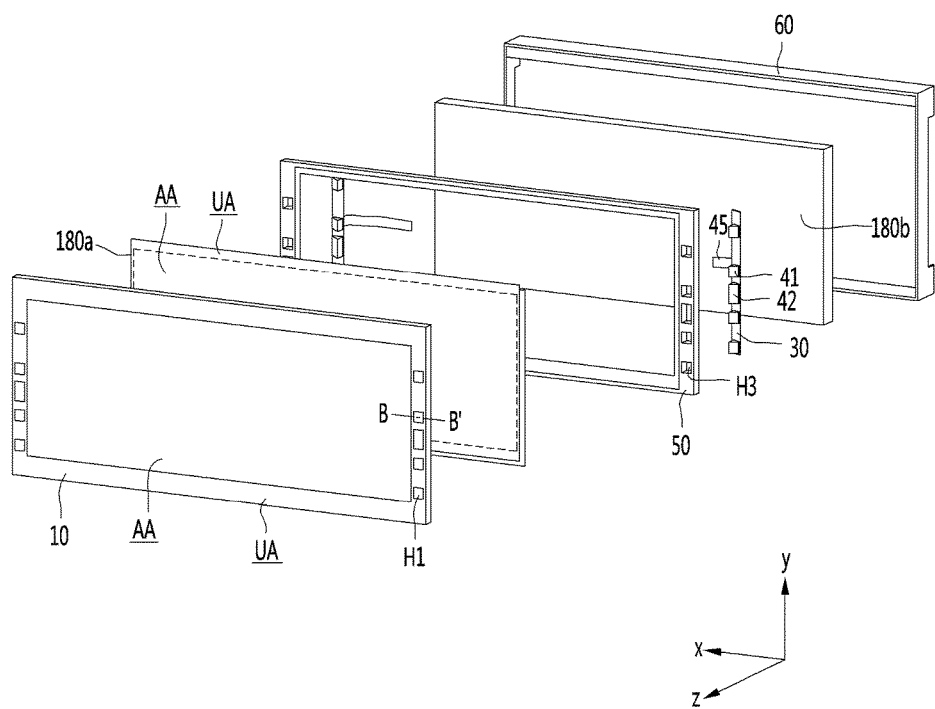
FIGS. 4A to 4C are diagrams illustrating another particular example of the display device of FIG. 1.
Figure 4B:
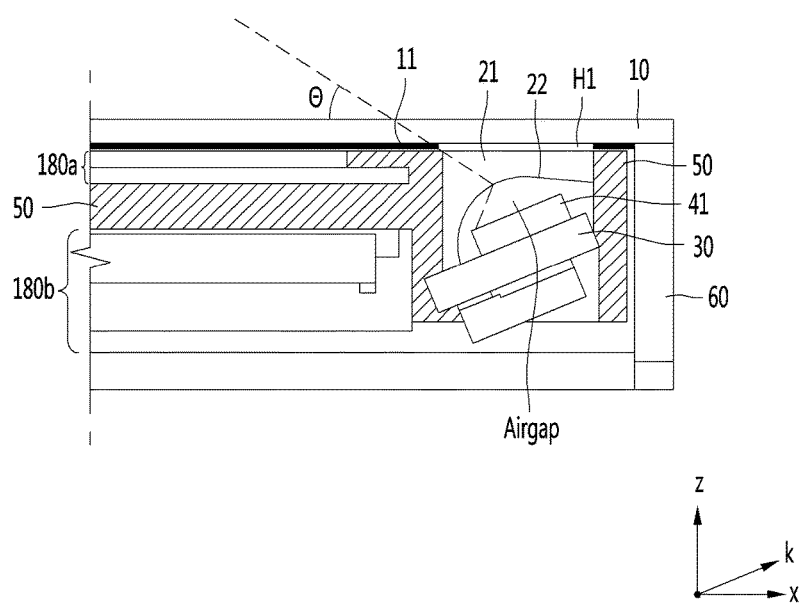
Figure 4C:
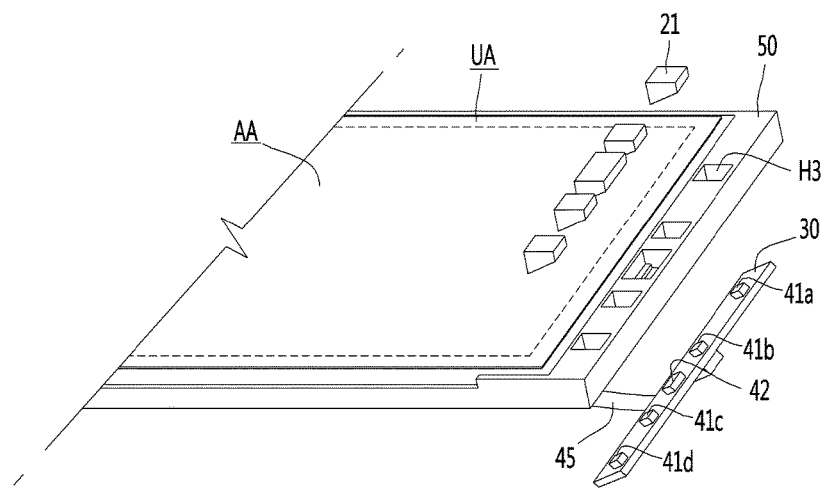

FIG. 4A is an exploded perspective view of the display device 100, FIG. 4B is a cross-sectional view of line B-B' in FIG. 4A, and FIG. 4C is a detailed perspective view of the light sensor unit 121 in the display device 100. Referring to FIGS. 4A to 4C, the display device 100 may include the touch window 10, the touch sensor unit 126 disposed under the touch window 10, the display unit 180, the bezel frame 50 that supports the display unit 180, the light sensor unit 121 disposed under the touch window 10, and the front casing 60.

In addition, the touch window 10 may include the active area AA and the unactive area UA. Specifically, the active area AA of the touch window 10 may be transparent in order to show an image displayed on the display unit 180. In addition, the unactive area UA of the touch window 10 may be opaque in order not to show various components that are disposed thereunder. Thus, the opaque printed layer 11 can be disposed on the unactive area UA of the touch window 10.

However, the printed layer 11 may not be disposed on at least a portion of the unactive area UA. That is, the printed layer 11 may include the first hole H1 can be disposed at a position corresponding to the light output unit 41 and the light receiving unit 42 of the light sensor unit 121. That is, the first hole H1 of the printed layer 11 can be disposed to overlap the light output unit 41 and the light receiving unit 42.

The touch sensor unit 126 can be disposed under such a touch window 10 and include the active area AA, and the active area AA of the touch sensor unit 126 can be disposed to overlap the active area AA of the touch window 10 to sense the direct touch and/or floating touch of an input tool. For example, an electrode that senses a touch on the touch sensor unit 126 can be disposed on the active area AA.

In addition, the touch sensor unit 126 may include the unactive area UA, and the unactive area UA of the touch sensor unit 126 may be smaller than the size of the unactive area UA of the touch window 10. Thus, an empty space may be formed on a side of the unactive area UA of the touch sensor unit 126.

In addition, the display unit 180 can be disposed under the touch sensor unit 126. However, the display unit 180 may include the liquid crystal panel 180a and the backlight unit 180b.

Such a display unit 180 may include the active area AA and the unactive area UA. Specifically, the active area AA of the display unit 180 is an area that displays an image, and can have a size corresponding to the active area AA of the touch window 10. In addition, the unactive area UA of the display unit 180 is an area on which a wiring electrode is disposed, and may be smaller than the unactive area UA of the touch window 10. Thus, an empty space may be formed on a side of the unactive area UA of the touch sensor unit 126.

In addition, the bezel frame 50 that supports the liquid crystal panel 180a and the backlight unit 180b may be further disposed. Further, such a bezel frame 50 may be larger than the active area AA of the touch window 10 and smaller than the unactive area UA. In addition, an empty space may be formed through the expansion from the unactive area UA of the bezel frame 50, and the light sensor unit 121 can be disposed in the empty space. That is, by disposing the light sensor unit 121 in an existing component, the bezel frame 50 without a separate frame, it is possible to decrease manufacturing costs and reduce the size of bezel.

Also, since the bezel frame is large and fixed firmly to the front casing 60, there is little impact on vibration transmitted to the display device 100 and thus it is possible to stably support the light sensor unit 121. Further, when the display device 100 is installed in a vehicle, vibration transmitted from the vehicle may occur, in which case the bezel frame 50 may cancel such vibration to enhance precision in sensing by the light sensor unit 121.

That is, the display device 100 may dispose the light sensor unit 121 in the empty space of the unactive area UA of the bezel frame 50 without using the separate noise reducing frame 20. Further, the bezel frame 50 may be expanded toward the unactive area UA to form a space for disposing the light sensor unit 121, and there may be a sidewall between the light sensor unit 121 and the display unit 180 to block interference between them.

In addition, the bezel frame 50 of the unactive area UA can have a third hole H3 for light transmission, and such a third hole H3 may correspond to the first hole H1 of the printed layer 11. In addition, the lens 21 can be disposed in the third hole H3 of the noise reducing frame 20. That is, the lens 21 may be inserted in the third hole H3 to cover the third hole H3.

Such a lens 21 is transparent and thus may transmit light. Further, the lens 21 may change the route of light from the light output unit 41 toward the active area AA in order to guide reflected light to the light receiving unit 42. Specifically, the lens 21 may include the concave surface 22. For example, the internal surface 22 of the lens 21 may be formed in a concave shape to enable the light output from the light output unit 41 to be emitted so that the light is further spread toward the active area AA. Likewise, the concave surface 22 enables the light reflected from the input tool to be collected by the light receiving unit 42 through the lens 21 to be capable of enhancing precision in proximity sensing and decreasing the size of the light sensor unit 121.

The light sensor unit 121 may include the light output unit 41, the light receiving unit 42, the lens 21, and the light sensor substrate 30. In addition, the light output unit 41 may output e.g., infrared (IR) light in order to sense an input tool that is placed on the top surface of the active area AA. Also, the light receiving unit 42 may receive scattered or reflected light when the light output from the light output unit 41 is reflected from the input tool on the top surface of the active area AA.

At least one light output unit 41 and at least one light receiving unit 42 can be disposed on the light sensor substrate 30, and the light sensor wiring 45 that supplies power to the light output unit 41 and to the receiving unit 42 and transmits information sensed from the light receiving unit 42 may be connected thereto.

The sidewalls of the bezel frame 20 of the unactive area UA may enhance the linearity of light output from the light output unit 41 to guide the light upwards, collect the light reflected from the input tool, and block noise, such as light emitted from the display unit 180.

Specifically, since the bezel frame 50 may include sidewalls between which there is a space, and the light sensor substrate 30 can be disposed between the sidewalls, an internal spaced surrounded by the light sensor substrate 30 and the bezel frame can be formed. In addition, the light output unit 41 and the light receiving unit 42 can be disposed on the light sensor substrate in the internal space.

Further, the light sensor substrate 30 can be disposed at an angle. Specifically, the light sensor substrate 30 can be disposed at an angle to the touch window 10. More specifically, the top surface of the light sensor substrate 30 can have a slope with respect to the top surface of the touch window 10.

For example, when the top surface of the active area AA is defined as a horizontal plane, the top surface of the light sensor substrate 30 may be at an angle to the horizontal plane. In a side view, a first end in the length direction of the light sensor substrate 30 can be disposed at a higher position than a second end in the length direction.

In this instance, the tilt direction (k axis) of the light sensor substrate 30 may be a direction that enables the top surface of the light sensor substrate 30 to face the active area AA. That is, the second end of the light sensor substrate 30 can be disposed toward the active area AA and the first end of the light sensor substrate 30 can be disposed at an edge.

Thus, the light output from the light output unit 41 disposed on the top surface of the light sensor substrate 30 may be output toward the active area AA. Furthermore, the light output toward the active area AA can be emitted through the concave surface 22 of the lens 21 to be further bent toward the active area AA. Thus, since output light may evenly cover the active area AA, the number of the light output units 41 may decrease. Since a similar optical property may also be applied to the light reflected from the input tool, the light receiving unit 42 may effectively collect reflected light.

As described earlier, the light output unit 41 and the light receiving unit 42 may be surrounded by the bezel frame 50, the light sensor substrate 30, and the lens 21. In addition, air gaps may be formed between the lens 21 and the light output unit 41 and between the lens 21 and the light receiving unit 42. In this instance, the air gap between the light output unit 41 and the lens may be larger than that between the light receiving unit 42 and the lens 21. Thus, the light output unit 41 may perform light output more efficiently and the light receiving unit 42 may perform light reception more efficiently.

In addition, the front casing 60 may support the touch window 10, the bezel frame 50, and the light sensor unit 121 as described earlier. Specifically, the touch window 10 can be disposed on the front casing 60 to form an internal space, and the bezel frame 50 can be disposed in the internal space. In addition, the front casing 60 may support the bottom surface of the light sensor substrate 30, a surface thereof that supports the light sensor substrate 30 may be formed as a slope corresponding to the light sensor substrate 30, but the embodiment is not limited thereto.

Since the light sensor substrate 30 is disposed at an angle and the lens 21 includes the concave surface 22, the light sensor unit 121 according to such a particular embodiment may enable light to be evenly transmitted onto the active area AA. Also, it is possible to dispose the light sensor unit 121 at the bezel frame 50 to further decrease the size of bezel and stably support the light sensor unit 121. Thus, since the numbers of the light output units 41 and the light receiving units 42 may decrease in addition to resolution enhancement and it is possible to dispose the light sensor unit 121 only on a portion of the unactive area UA, there are advantages in that it is possible to reduce manufacturing costs and decrease the size of bezel.

Figure 5:
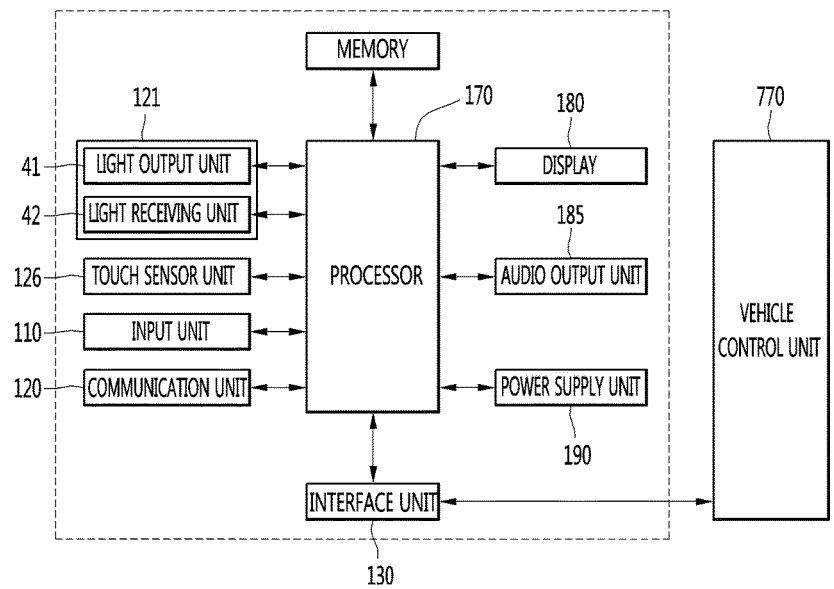
FIG. 5 is an internal block diagram of the display device of FIG. 1.

In the following, the operation of the display device 100 according to the above-described embodiment is described in detail with reference to FIGS. 5 to 11. Referring to FIG. 5, the display device 100 according to an embodiment may include the above-described light sensor unit 121, the touch sensor unit 126, and the display unit 180 and include an input unit 110, a communication unit 120, an interface unit 130, a memory 140, a processor 170, an audio output unit 185, and a power supply unit 190.

Specifically, the display device 100 may include the input unit 110 that senses a user's input. The input unit 110 may include a button so that a user may turn on/off the display device 100 through the input unit 110. In addition, an input signal through the input unit 110 may be transmitted to the processor 170.

Next, the display device 100 may include the communication unit 120 that communicates with another vehicle, a mobile terminal, a server, etc. The display device 100 may receive navigation information and/or traffic information through the communication unit 120.

Specifically, the communication unit 120 may exchange data with the mobile terminal or the server wirelessly. In particular, the communication unit 120 may wirelessly exchange data with the mobile terminal of a vehicle driver. The wireless data communication scheme may include various data communication schemes, such as Bluetooth, WiFi, Direct WiFi, APiX, or NFC schemes. Also, when a user gets in the vehicle, the mobile terminal of the user and the display 100 may also perform pairing automatically or by the execution of an application by the user.

Next, the display device 100 may include the interface unit that receives vehicle related data or transmits a signal processed or generated by the processor 170 to the outside. Specifically, the display device 100 may receive navigation information and/or sensor information through the interface unit 130.

Thus, the interface unit 130 may perform data communication with the control unit 770 in the vehicle by wired or wireless communication scheme. The interface unit 130 may receive navigation information through data communication with the control unit 770 and/or a separate navigation device.

Also, the interface unit 130 may receive sensor information from the control unit 770. In this example, the sensor information may include at least one of vehicle direction information, position information, speed information, acceleration information, tilt information, forward/backward movement information, fuel information, information on the distance to the front and rear vehicles, information on the distance between a vehicle and a lane, and turn signal information.

Next, the memory 140 may store various pieces of data for the overall operations of the display device 100, such as programs for processing or controlling by the processor 170. The memory 140 may be various storage devices, such as ROMs, RAMs, EPROMs, flash drives, hard drives, etc. that are hardware.

Also, the display device 100 may further include the audio output unit 185 and the power supply unit. Specifically, in addition to display, the audio output unit 185 may output, through sound, a description on the function of the display device 100, a message checking whether to execute the function or the like. Lastly, the display device 100 may include the processor 170 that controls the overall operations of each unit in the display device 100.

The processor 170 may be implemented by using at least one of an application specific integrated circuit (ASIC), a digital signal processor (DSP), a digital signal processing device (DSPD), a programmable logic device (PLD), a field programmable gate array (FPGA), a controller, a microcontroller, a microprocessor 170, and electrical units for executing other functions.

In the following, the processes or sensing and detecting, by the light sensor unit 121, the touch sensor unit 126, and the processor 170, a proximity touch, a floating touch, and a direct touch are described. In particular, when a user input tool 400 is placed within a first distance L1 (in FIG. 6A) from the display device 100, the light output from the light output unit 41 in the light sensor unit 121 of the display device 100 is reflected or scattered by the user input tool and received by the light receiving unit 42.

The processor 170 may calculate position information corresponding to the position of the user input tool based on the light received by the light receiving unit 42. In particular, it is possible to calculate x axis and y axis information on the display device 100. Also, it is possible to approximately calculate z axis information, the distance between the display device 100 and the user input tool, based on the intensity of the received light.

When the user input tool gradually approaches the display device, the processor 170 may continue to calculate x axis, y axis and z axis information on the user input tool based on the light received by the light receiving unit 42. In this instance, the z axis information may gradually decrease.

When the user input tool approaches to be within a second distance L2 (in FIG. 6A) closer to the display in comparison the first distance L1 (in FIG. 6A), power may be applied to the touch sensor unit 126 and thus an operation may be performed. That is, when the user input tool is not within the second distance, the touch sensor unit 126 may not operate and thus it is possible to decrease unnecessary power consumption.

The touch sensor unit 126 can sense a floating touch and a direct touch and it may include an electrode array and an MCU. When the touch sensor unit 126 operates, an electrical signal is supplied to the electrode array so that an electric field is formed on the electrode array.

When the user input tool approaches to be within a third distance L3 (in FIG. 6A) closer to the display in comparison to the second distance L2 (in FIG. 6A), the electric field on the top surface of the display device 100 has a variation in capacitance and the touch sensor unit 126 senses the variation. In addition, it is possible to calculate x axis and y axis information on a floating touch input based on the sensed variation in capacitance. Also, it is possible to calculate z axis information, the distance between the display device 100 and the user input tool, based on the intensity of the varying capacitance.

In this instance, it is possible to alter grouping for the electrode arrays in the touch sensor unit 126 based on the distance information on the user input tool that is calculated based on the light sensor unit 121, i.e., based on z axis information. It is possible to decrease the size of a group of electrode arrays with a decrease in distance to a display.

That is, it is possible to alter the size of touch sensing cells for the electrode array in the touch sensor unit 126 based on the distance information on the user input tool that is calculated based on the light sensor unit 121, i.e., based on z axis information. For example, when the distance to the user input tool is within the second distance L2 (in FIG. 6A), the size of touch sensor cells (grouping electrodes) is a first size by the grouping of the electrode arrays and may be a size corresponding to 9 electrode cells, and when the distance to the user input tool is within the third distance L3 (in FIG. 6A) shorter than the second distance L2 (in FIG. 6A), the size of touch sensor cells (grouping electrodes) is a second size, which may be a size corresponding to 4 electrode cells.

In another example, when the distance to the user input tool is within the second distance L2 (in FIG. 6A), the size of touch sensor cells (grouping electrodes) is a first size by the grouping of the electrode arrays and may be a size corresponding to 4 electrode cells, and when the distance to the user input tool is within the third distance L3 (in FIG. 6A) shorter than the second distance L2 (in FIG. 6A), the size of touch sensor cells (grouping electrodes) is a second size, which may be a size corresponding to 1 electrode cell.

That is, it is possible to decrease the size of touch sensor cells with a decrease in distance to a display. The variation in size of touch sensing cells (grouping electrodes) may be performed by a variation in electrical signal applied to the electrode array.

For example, when the size of the touch sensing cells (grouping electrodes) is a size corresponding to 9 electrode cells, it is possible to apply an electrical signal only to a first horizontal electrode and a fourth horizontal electrode among first to fourth horizontal electrodes and apply an electrical signal only to a first vertical electrode and a fourth vertical electrode among first to fourth vertical electrodes to set the size of touch sensing cells (grouping electrodes) corresponding to a size that corresponds to 9 electrode cells.

In another example, when the size of the touch sensing cells (grouping electrodes) is a size corresponding to 4 electrode cells, it is possible to apply an electrical signal only to a first horizontal electrode and a third horizontal electrode among first to third horizontal electrodes and apply an electrical signal only to a first vertical electrode and a third vertical electrode among first to third vertical electrodes to set the size of touch sensing cells (grouping electrodes) corresponding to a size that corresponds to 4 electrode cells.

In another example, when the size of the touch sensing cells (grouping electrodes) is a size corresponding to 1 electrode cell, it is possible to apply an electrical signal to each horizontal electrode and each vertical electrode to set the size of touch sensing cells (grouping electrodes) corresponding to a size that corresponds to 1 electrode cell.

As a result, the size of power consumed by the electrode array in the touch sensor unit 126 may vary according to a distance to the user input tool. The size of power consumed by the electrode array in the touch sensor unit 126 increases with a decrease in distance to the user input tool.

When the user input tool, especially an input tool finger approaches to be within in the third distance L3 (in FIG. 6A), the touch sensor unit 126 senses a variation in capacitance by the user input tool finger on the electric field on the top surface of the display device 100. In addition, the processor 170 may calculate x axis and y axis information on a floating touch input based on the sensed variation in capacitance. Also, it is possible to calculate z axis information, the distance between the display device 100 and the user finger, based on the intensity of the varying capacitance.

When a capacitance variation signal for the user input tool is sensed from some of a plurality of set touch sensing cells when the user input tool is placed within the second distance L2 (in FIG. 6A), processor 170 can calculate position information on the user input tool based on one of the sensed capacitance variation signals that has the largest intensity. That is, it is possible to recognize only one of a plurality of floating touches. Alternatively, it is also possible to recognize all of the plurality of floating touches. However, when recognizing the plurality of floating touches, it is also possible to recognize only capacitance variation signals that have intensity equal to or higher than a predetermined value.

When the user input tool is placed on the unactive area UA when the user input tool is placed within the first distance L1 (in FIG. 6A), the processor 170 may calculate position information on the user input tool based on output light and received light that is received by the light sensor unit 121. That is, when position information on the user input tool is calculated by the light sensor unit 121, the processor 170 can calculate position information even when the user input tool is placed on not only the active area AA but also the unactive area UA around the active area AA. The reason is that the light sensor unit 121 is disposed on the unactive area UA.

The touch sensor unit 126 can be disposed on the top surface or bottom surface of a display. Thus, when the user input tool is within the second distance L2 (in FIG. 6A) and placed on an area corresponding to the active area AA, it is possible to recognize the user input tool, but when the user input tool is placed on the unactive area UA around the active area AA, the user input tool may not be accurately recognized.

That is, a range of an area based on x axis and y axis that may be recognized by the light sensor unit 121 is wider than a range of an area based on x axis and y axis that may be recognized by the touch sensor unit 126. When the user input tool moves from the first distance to the second distance, the processor 170 may output an indicator representing that a touch input is possible. In this instance, the indicator may include predetermined sound that is output through the audio output unit 185, and a predetermined image that is output through a display.

The processor 170 may enable a corresponding menu to be displayed on a display based on calculated position information on the user input tool. The processor 170 may highlight a specific item on the menu displayed on the display, based on calculated position information on the user input tool. The processor 170 may select or highlight a specific item on the menu displayed on the display, based on calculated position information on the user input tool.

When the calculated distance to the user input tool is within the second distance, the processor 170 may display a predetermined menu on the display, and when the calculated distance to the user input tool is within the third distance, it is possible select or highlight a specific item on the menu displayed on the display, based on the calculated position information on the user input tool.

The display unit 180 may correspond to at least one of a liquid crystal display (LCD), a thin film transistor-liquid crystal display (TFT LCD), an organic light-emitting diode (OLED), a flexible display, a 3D display, and an e-ink display. The power supply unit 190 may supply power required for the operation of each component by the control of the processor 170.

Figure 6A:
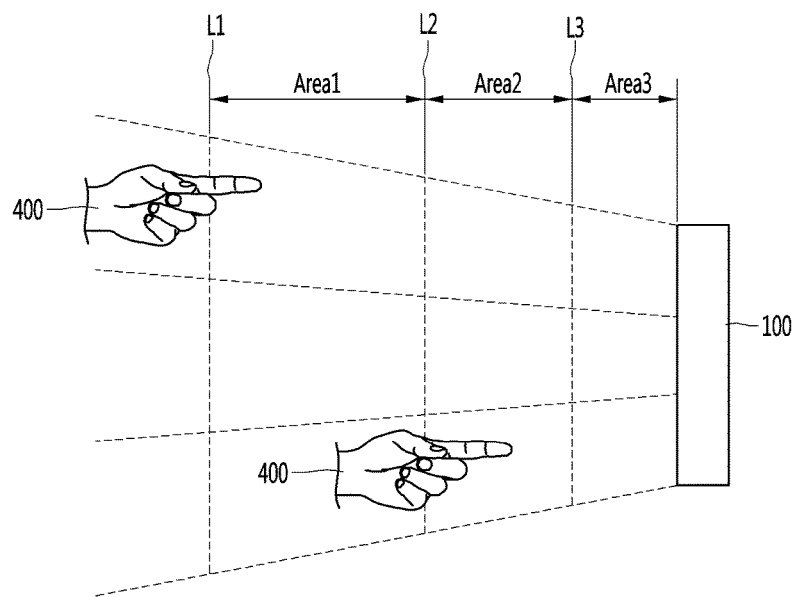
FIGS. 6A to 6B are diagrams illustrating the user's hand recognition of the display device of FIG. 1.
Figure 6B:
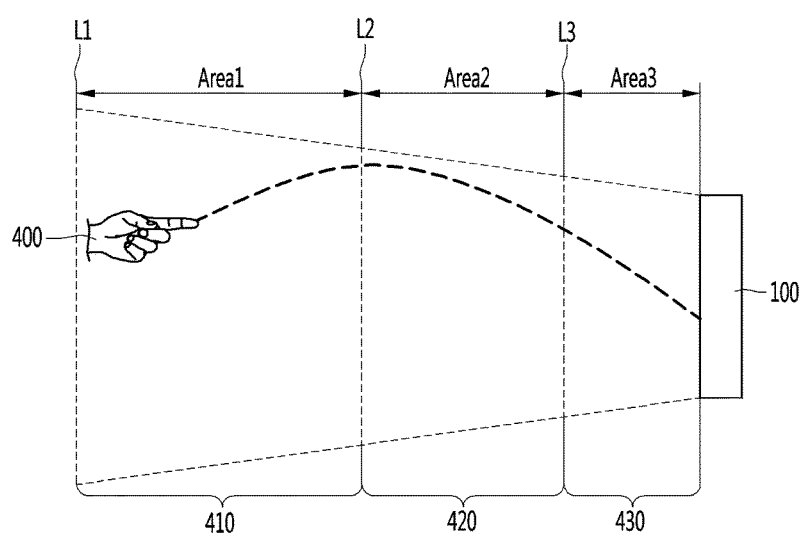

FIGS. 6A to 6B are diagrams illustrating the user input tool recognition of the display device of FIG. 1. Referring to FIGS. 6A and 6B, FIG. 6A illustrates that the user input tool 400 is placed on the top surface of the display device 100 and gradually approaches.

When the user input tool 400 gradually approaches When it is placed on the top surface of the display device 100, the display device 100 according to an embodiment can recognize all routes, sections and positions of the input tool until a touch input is performed (hand detection), and when the distance is shorter, it can recognize an input tool finger (finger detection).

The approaching routes of the user input tool to the display device 100 in the present disclosure may be divided as shown in FIG. 6B. That is, the routes may be divided into a first area Area1 410 between the first distance L1 and the second distance L2, a second area Area2 420 between the second distance L2 and the third distance L3, and a third area Area3 430 within the third distance L3.

The first area Area1 is an output light dispersion area on which the light output from the light sensor unit 121 is dispersed. The first area Area1 is an area farthest from the display device 100 and may be named as an emerging area. The second area Area2 and the third area Area3 are electric field dispersion areas on which the electric field generated from the touch sensor unit is dispersed by the operation of the touch sensor unit 126.

Further, the second area Area2 may be an area on which the touch sensor unit 126 operates corresponding to the calculated distance, based on the output light output from the light sensor unit 121 and received light. Thus, the second area may be named as the approaching area.

The second area Area2 and the third area Area3 are electric field dispersion areas and can have a floating touch but different in size of touch sensing cells. That is, the size of the touch sensing cells of the third area Area3 may be smaller than that of the second area Area2, thus it is possible to more minutely discern position information on the user input tool.

As a result, the third area Area3 may point or target the user input tool. Thus, the third area Area3 may be named as a targeting area. The light output from the light sensor unit 121 may also be dispersed to the second area Area2. Thus, the second area Area2 may be an overlap area on which the electric field by the touch sensor unit 126 and the output light overlap.

As a result, the display device 100 may detect the motion of the user input tool (hand motion) in the first area Area1 through the light sensor unit 121 and detect the presence of the user input tool (hand detection) in the second area Area2 and the third area Area3 through the touch sensor unit 126.

FIG. 7 is a diagram illustrating the operations of the light output unit 41 and the touch sensor unit 126. FIG. 7 illustrates the distribution of output light on the first area Area1 and the second area Area2 as described in FIG. 6B. Further, FIG. 7 illustrates that the intensity of the output light is higher around the display device 100 but the output light is distributed over all areas of the top surface of the display device 100.

FIG. 7 also illustrates the distribution of electric field on the second area Area2 and the third area Area3 as described in FIG. 6B. As described above, since the electrical signal is supplied to the electrode array in the touch sensor unit 126, the electric field is distributed over all areas of the top surface of the display device 100.

As such, the display device 100 according to an embodiment has no blind spot upon recognition of the user input tool in a space on the top surface of the display device 100 by a combination of the light sensor unit 121 and the touch sensor unit 121 for detecting a floating touch input, based on infrared light. Also, it is possible to obtain x axis, y axis and z axis information on the user input tool, such as a user input tool. Also, a user input tool detection speed is fast and the display device can also be used in a large display device 100. Also, since it selectively operates the touch sensor unit 126, it is possible to decrease power consumption.

Figure 8A:
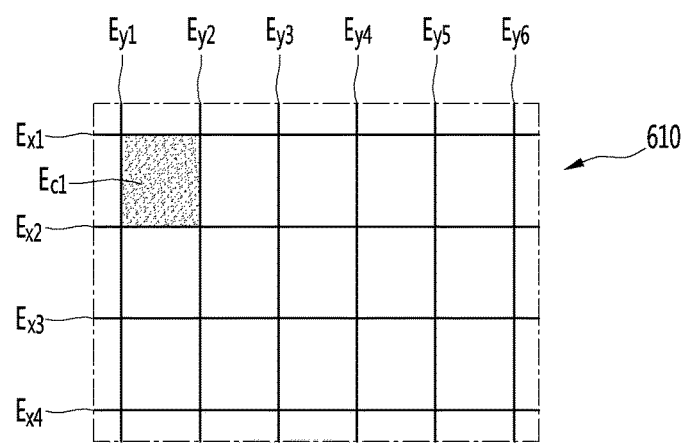
FIGS. 8A to 8C are diagrams illustrating the operation of a touch sensor unit in FIG. 5.
Figure 8B:
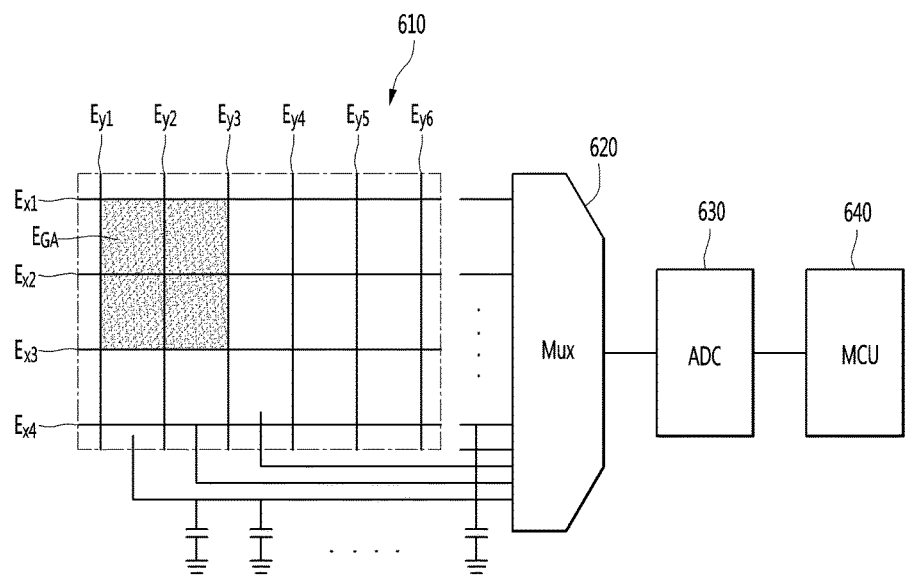
Figure 8C:
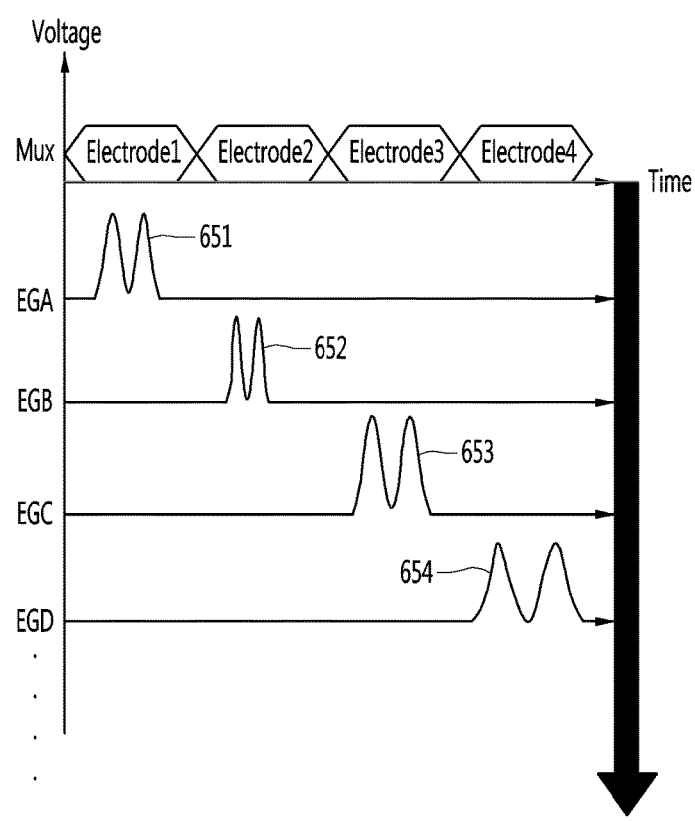

FIGS. 8A to 8C are diagrams illustrating the operation of the touch sensor unit 126. In addition, FIG. 8A illustrates a portion of an electrode array 610 in the touch sensor unit 126. The electrode array 610 may include horizontal electrodes Ex1, Ex2, Ex3, and Ex4 and vertical electrodes Ey1, Ey2, Ey3, Ey4, Ey5, and Ey6.

The processor 170 may alter the grouping of the electrode array in the touch sensor unit 126 based on approximate z axis information calculated based on light received from the light sensor unit 121. For example, when the distance to the user input tool is within the third distance L3, i.e., within the third area Area3 as described above, the size of the touch sensing cells (grouping electrodes) may be a size corresponding to 1 electrode cell Ec1 as shown in FIG. 8A.

As another example, when the distance to the user input tool is between the second distance L2 and the third distance L3, i.e., within the second area A2 as described above, the size of the touch sensing cells (grouping electrodes) may be a size corresponding to 4 electrode cell Electrode Group A as shown in FIG. 8B.

FIG. 8B illustrates a portion of the electrode array 610 in the touch sensor unit 126. Further, a variation in capacitance is sensed corresponding to 4 electrode cells Electrode Group A. A signal for a capacitance variation sensed by a plurality of electrode cells is muxed by a MUX 620, converted into a digital signal by an ADC 630 and signal-processed by an MCU 640. The MCU 640 may calculate x axis, y axis and z axis information on a floating touch input based on the digital signal obtained through conversion.

When in the size of touch sensing cells (grouping electrodes) is a size corresponding to 4 electrode cells as shown in FIG. 8B, the MCU 640 may apply an electrical signal only to a first horizontal electrode Ex1 and a third horizontal electrode Ex3 among the plurality of horizontal electrodes Ex1, Ex2, Ex3, and Ex4 and apply an electrical signal only to first, third, and fifth vertical electrodes Ey1, Ey3, and Ey5 among the plurality of vertical electrodes Ey1, Ey2, Ey3, Ey4, Ey5, and Ey6. Thus, the size of touch sensing cells (grouping electrodes) may be set corresponding to 4 electrode cells.

The MCU 640 may also be included in the above-described processor 170. The size of touch sensing cells (grouping electrodes) may be set corresponding to the user input tool or the position of user input tool finger, such as $1\lambda1$, $2\lambda2$, $3\lambda3$, and $2\lambda7$.

Next, FIG. 8C illustrates a capacitance variation sensed by the electrode array 610 in the touch sensor unit 126. FIG. 8C illustrates that capacitance variation signals 651, 652, 653, and 654 sensed at a plurality of electrode cells Electrode Groups A, B, C, D . . . are sensed by a time division sensing method. The MUX 620 may mux these signals 651, 652, 653, and 654 to output the muxed analog signals.

Figure 9:
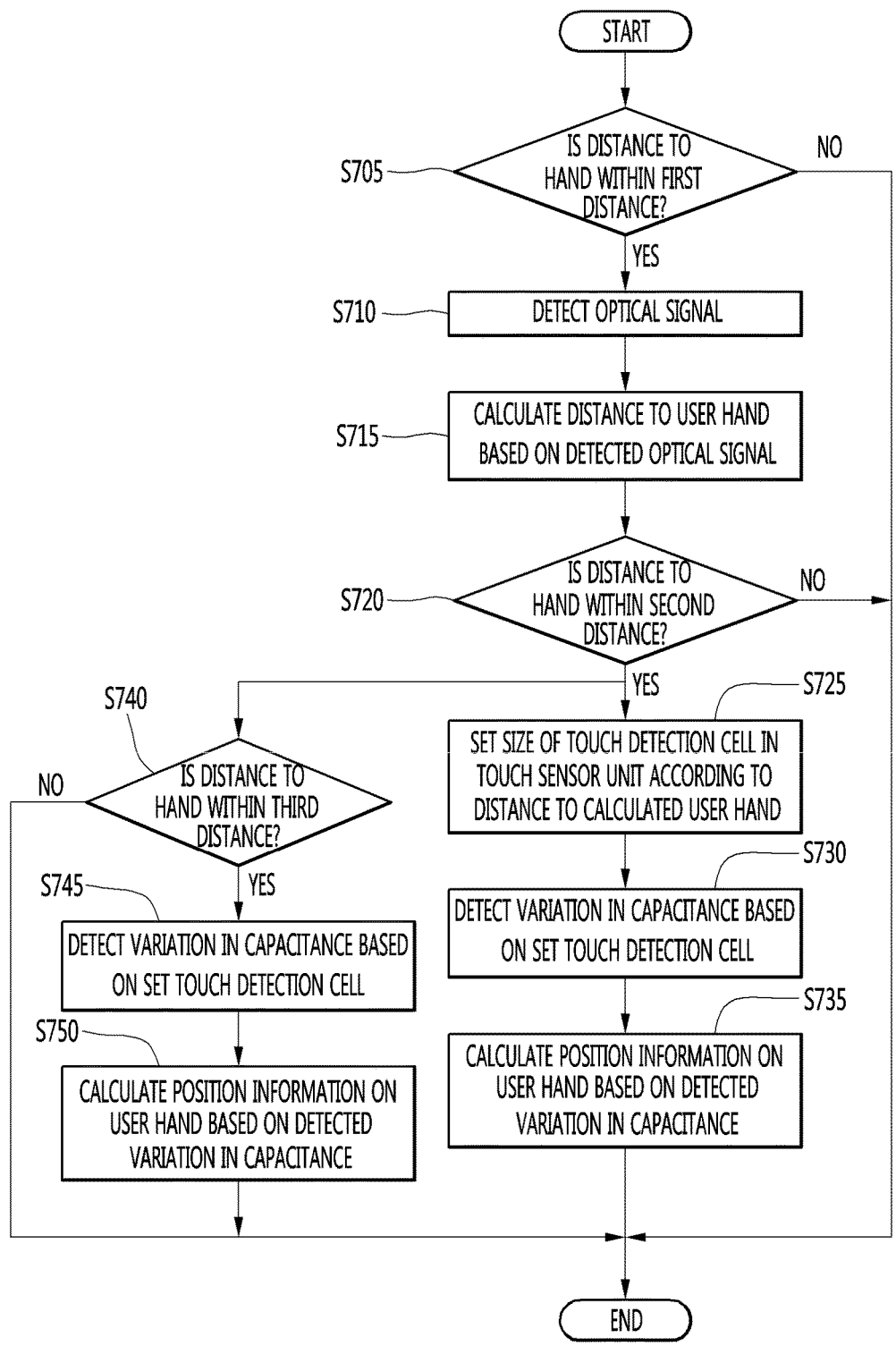
FIG. 9 is a flowchart of the operating method of a display device according to an embodiment.

FIG. 9 is a flowchart of the operating method of the display device 100 for a vehicle according to an embodiment. Referring to FIG. 9, In addition, the light sensor units 121 and 221 in the display device 100 output light to be output. In addition, the light sensor units 121 and 221 in the display device 100 for the vehicle output light to be output and receive received light that corresponds to the output light.

Next, the processor 170 determines whether a distance to a user input tool is within a first distance in step S705. Since the distance to the user input tool is within the first distance if positive, the intensity of the received light may be equal or higher than a predetermined value and thus the processor 170 may perform signal processing.

Thus, when it is possible to recognize the received light, the processor 170 receives the received light and detects an optical signal in step S710. The processor 170 of the display device 100 calculates the distance to the user input tool based on the optical signal detected at the light sensor unit 121 in step S715.

The processor 170 may calculate position information corresponding to the position of the user input tool based on an electrical signal from the light sensor unit 121. In particular, it is possible to calculate x axis and y axis information on the display device 100. Also, it is possible to approximately calculate z axis information, the distance between the display device 100 and the user input tool, based on the intensity (size or amplitude) of the electrical signal from the light sensor unit 121.

In addition, the processor 170 of the display device 100 determines whether the user input tool continues to approach and the distance to the user input tool calculated based on the light sensor unit 121 is within a second distance in step S720. In addition, if positive, the processor 170 operates the touch sensor unit 126 and sets the size of touch sensing cells in the touch sensor unit 126 according to the calculated distance to the user input tool in step S725.

Here, the second distance may correspond to the second area as described above. As described above, the second area may be an area on which the output light output from the light sensor unit 121 and an electric field area by the touch sensor unit 126 overlap. For example, when the distance to the user input tool is between the second distance L2 and the third distance l3, the size of touch sensing cells (grouping electrodes) may be a size corresponding to 4 electrode cells by the grouping of an electrode array.

In addition, the touch sensor unit 126 senses a capacitance variation by the user input tool based on the touch sensing cells set to 4 electrode cells in step S730. The touch sensor unit 126 senses a capacitance variation by the user input tool finger on the electric field on the top surface of the display device 100.

In addition, the processor 170 calculates position information on the user input tool based on the sensed capacitance variation in step S735. That is, the processor 170 may calculate x axis and y axis information on a floating touch input based on the sensed capacitance variation. Also, it is possible to calculate z axis information, the distance between the display device 100 and the user input tool finger, based on the intensity of the varying capacitance. In this instance, x axis and y axis information may be information corresponding to the sizes of 4 touch sensing cells.

Next, in step S720, step S740 may also be performed when the distance to the user input tool calculated based on the optical signal is within the second distance. That is, the processor 170 may determine whether the calculated distance to the user input tool is within the third distance in step S740. In addition, if positive, the processor 170 sets so that touch sensing cells in the touch sensor unit 126 correspond to 1 electrode cell.

In addition, the touch sensor unit 126 senses a capacitance variation by the user input tool based on the set touch sensing cells in step S745. In addition, the processor 170 calculates position information on the user input tool based on the sensed capacitance variation in step S750. That is, the processor 170 may calculate x axis and y axis information on a floating touch input based on the sensed capacitance variation.

Also, it is possible to calculate z axis information, the distance between the display device 100 and the user input tool finger, based on the intensity of the varying capacitance. In this instance, x axis and y axis information may be information corresponding to the size of 1 touch sensing cell. Thus, when the user input tool is placed within the third area Area3 rather than the second area Area2, it is possible to discern position information more accurately.

Figure 10:
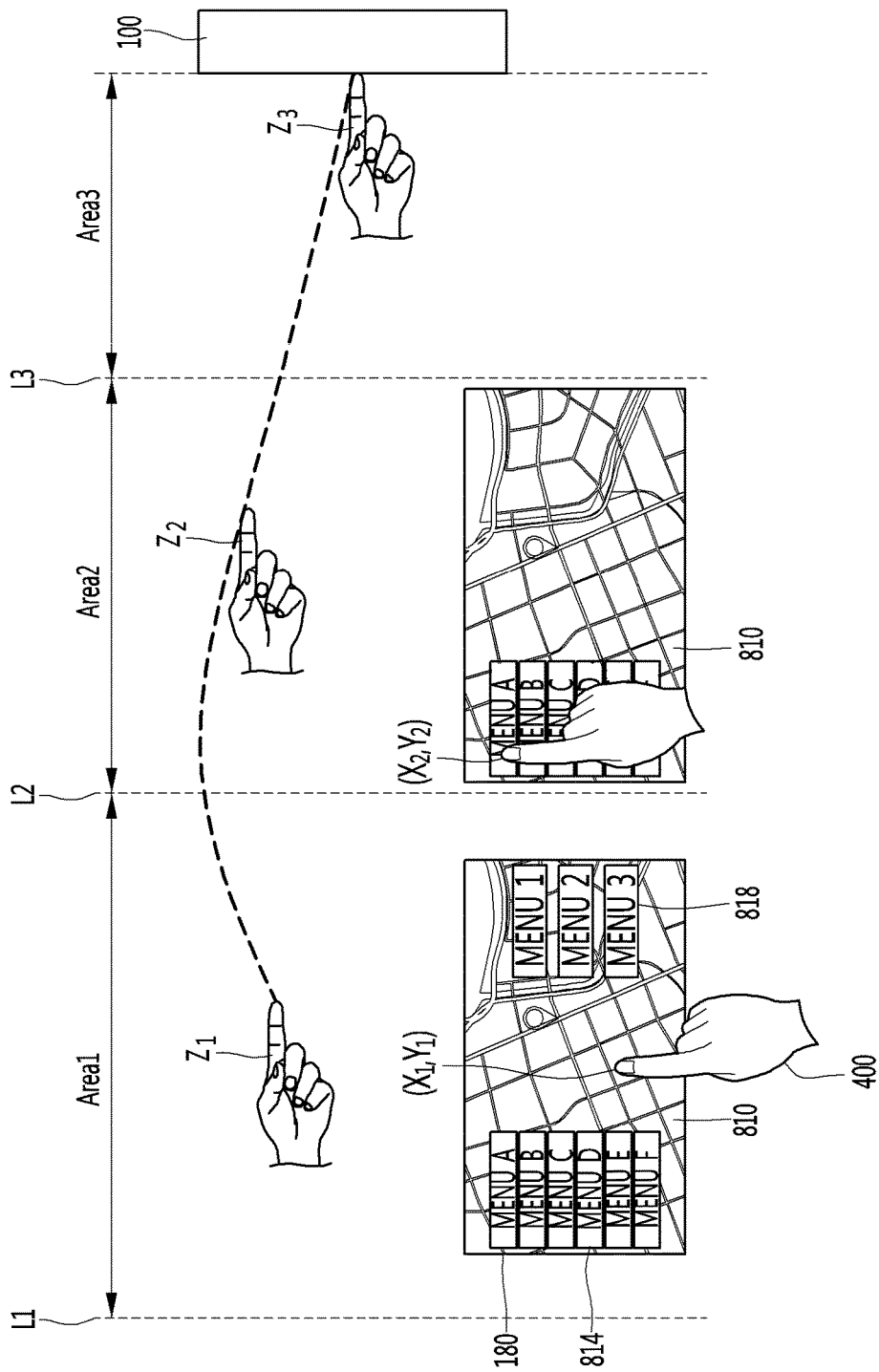
FIGS. 10 and 11 are diagrams illustrating the operating method of FIG. 9.
Figure 11:
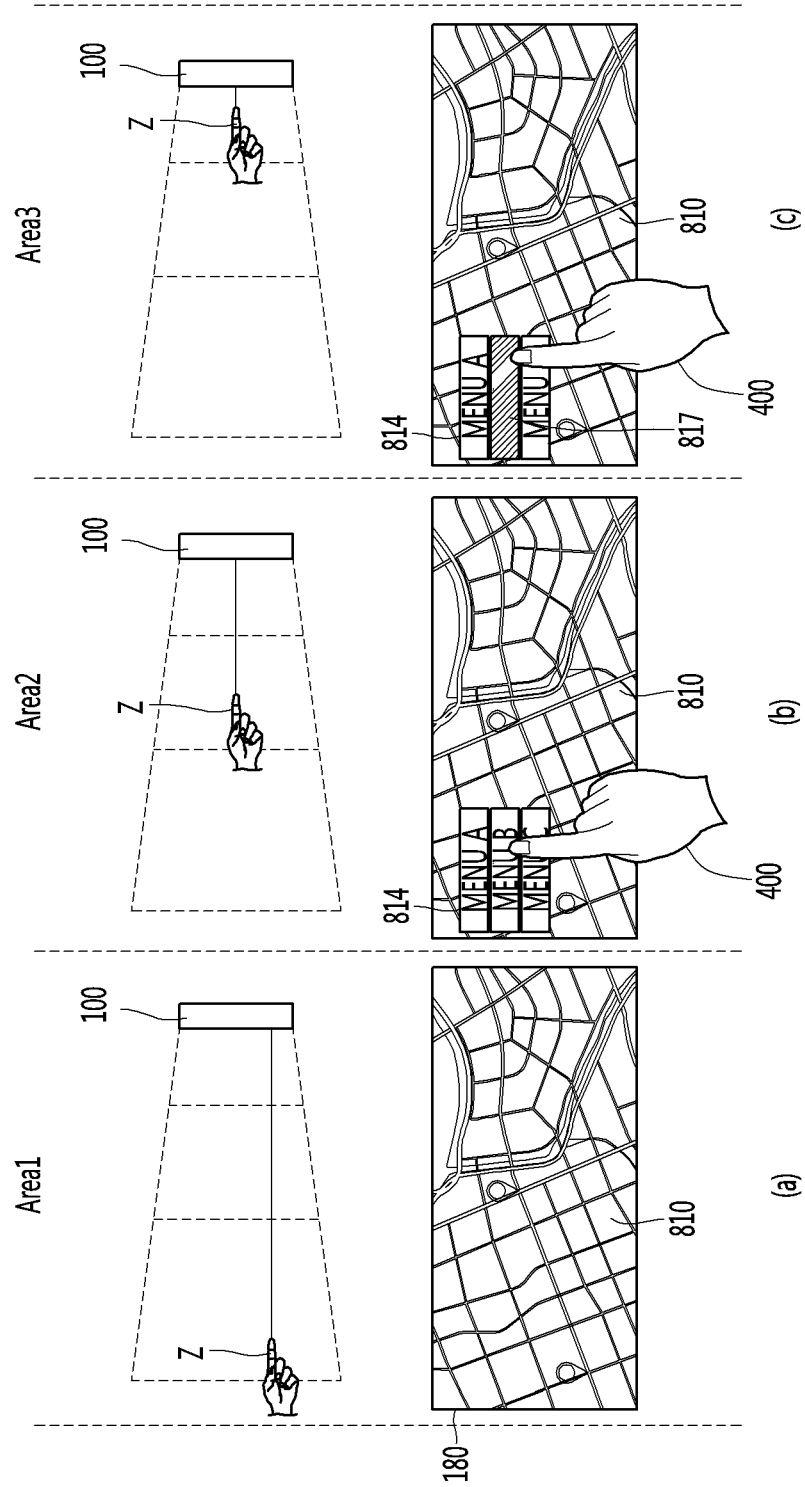

FIGS. 10 and 11 are diagrams illustrating the operating method of FIG. 9. FIGS. 10 and 11 illustrate that the display device 100 tracks the continuous operation of the user input tool.

Referring to FIG. 10, the processor 170 calculates and recognizes distance information z1 on the user input tool based on the operation of the light sensor unit 121, when the position x1, y1, z1 of the user input tool is placed on the first area Area1. In this instance, it is also possible to calculate x axis and y axis information x1, y1 in addition to z axis information.

When the position of the user input tool is placed on the first area Area1, the processor 170 may display a map 810 and first and second menus 814 and 818 on a display. Thus, even without a separate input operation, it is possible to automatically display the map 810 according to the position of the user input tool and thus user convenience may increase.

Next, the processor 170 calculates and recognizes distance information z2 on the user input tool based on the operation of the light sensor unit 121, when the position x2, y2, z2 of the user input tool gradually approaches and is placed on the second area Area2. In this instance, it is also possible to calculate x axis and y axis information x2, y2 in addition to z axis information.

The processor 170 may operate the touch sensor unit 126 when the position x2, y2, z2 of the user input tool gradually approaches and is placed on the second area Area2. Thus, the processor 170 can recognize position information x2, y2, z2 on the user input tool based on the capacitance sensed at the touch sensor unit 126.

In the case of the second area Area2, the processor 170 may obtain, through the touch sensor unit 126, more accurate position information than position information based on the light sensor unit 121. The size of touch sensing cells on the second area Area2 may correspond to 4 electrode cells and thus x axis and y axis information x2, y2 may be x axis and y axis information corresponding to 4 electrode cells.

When the user input tool is placed on the second area Area2, the processor 170 may display, on a display, a predetermined menu or only details related to position information on the input tool based on calculated position information on the user input tool.

FIGS. 11b and 11c illustrate that the second menu 818 that is not relevant is not displayed because position information on the user input tool is x2, y2, z2 and placed near the first menu 814. Thus, a user may concentrate on a desired menu. Next, when the position of the user input tool is placed on the third area Area3 or in contact with the display device 100 due to a gradual approach, the processor 170 can recognize a floating touch input or a direct touch input based on the touch sensor unit 126.

That is, it is possible to recognize position information x3, y3, z3 on the user input tool. In addition, a specific item in the first menu 814 may be selected. The size of touch sensing cells on the third area Area3 may correspond to 1 electrode cell and thus x axis and y axis information x3, y3 may be x axis and y axis information corresponding to 1 electrode cell.

Next, FIG. 11A illustrates that the map 810 is displayed on a display when the position of the user input tool is placed on the first area Area1. When the distance to the user input tool is za, the processor 170 calculates and recognizes distance information za on the user input tool based on the operation of the light sensor unit 121. In addition, only the map 810 may be displayed on the display based on calculated distance information on the user input tool.

Next, FIG. 11B illustrates that in addition to the map 810, the menu 814 is further displayed on the display when the position xb, yb, zb of the user input tool is placed on the second area Area2. Further, FIG. 11B illustrates that the menu 814 is displayed corresponding to the x coordinate and the y coordinate.

The processor 170 may operate the touch sensor unit 126 when distance information on the user input tool calculated based on the operation of the light sensor unit 121 is within the second distance L2. Thus, the processor 170 can recognize position information on the user input tool based on the capacitance sensed at the touch sensor unit 126.

When the user input tool moves from the first distance L1 to the second distance L2, the processor 170 may output an indicator representing that a touch input is possible. In this instance, the indicator may include predetermined sound that is output through the audio output unit 185, and a predetermined image that is output through a display.

The processor 170 may display a predetermined menu on the display based on position information on the user input tool when the user input tool is placed within the second distance. Further, it is possible to display a menu on an area corresponding to the position of the user input tool based on position information on the user input tool, x axis and y axis information. Thus, since a menu is easily displayed on the position of the user input tool while driving, user convenience may increase.

Next, FIG. 11C illustrates that a specific item 817 on the menu 814 displayed on the display is highlight when the position xb, yb, zc of the user input tool is placed on the third area Area3 when the user input tool is not in contact with the display. Further, FIG. 11C illustrates that the specific item 817 on the menu 814 is displayed corresponding to the x coordinate and the y coordinate. Thus, a user may easily select a menu item that he or she desires.

In FIG. 11C, the specific item 817 may also be immediately selected together with highlighting. Alternatively, the item may also be immediately selected without highlighting. As such, by selecting or highlighting the menu displayed on the display or the specific item on the menu according to the distance to the user input tool, menu selection or specific item selection on a menu in a vehicle that vibrates is easy. Thus, user convenience may increase.

Such a display device 100 is a breadthwise display device 100 and can have a shape suitable for the vehicle. In addition, since the light sensor unit 100 of the breadthwise display device 100 is disposed in a structure resistant to vibration, it is possible to precisely sense a proximity touch even in a shaking vehicle.

Figure 12:
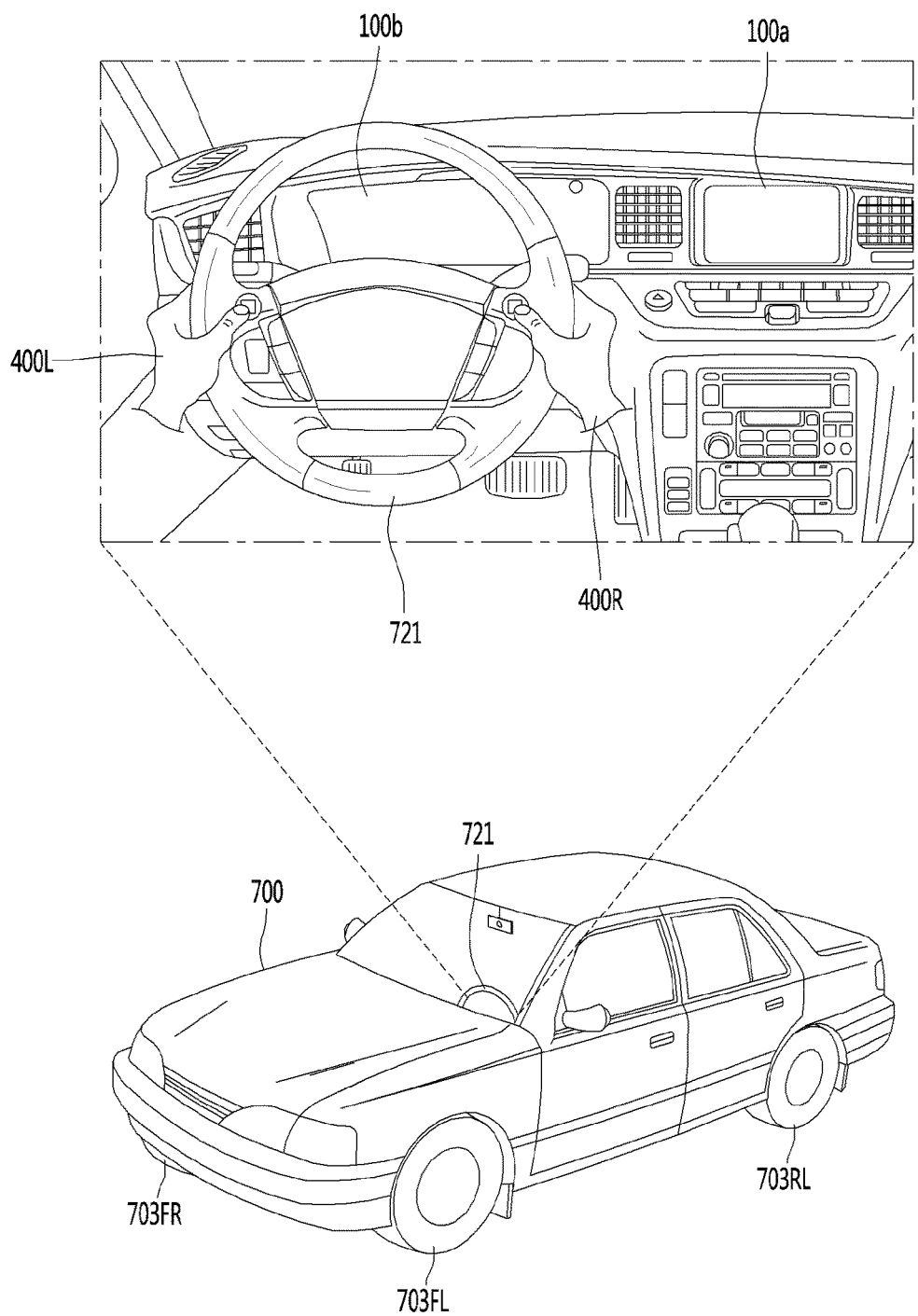
FIG. 12 is a diagram illustrating representing a vehicle that includes a display device according to an embodiment.

Specifically, referring to FIG. 12, a vehicle according to an embodiment may include wheels 703RF, 703FL, 703RL, . . . that rotate by a power source, a steering wheel for regulating the driving direction of the vehicle, and the display device 100 for providing information to a user.

The display device 100 according to the above-described embodiment is a breadthwise display and may be suitable for the display device 100 for a vehicle for displaying a lot of user information, such as a map, vehicle function information, and internal sensor information.

In addition, since the light sensor unit 100 of the breadthwise display device 100 is disposed in a structure resistant to vibration, it is possible to precisely sense a proximity touch even in a shaking vehicle. Also, by selecting or highlighting the menu displayed on the display or the specific item on the menu according to the distance to a user hand, it is possible to easily select the menu or the specific item on the menu within a vehicle that vibrates.

Thus, a vehicle according to an embodiment may dispose the above-described display device 100 in an audio video navigation (AVN) device and/or on the cluster of the top surface inside the vehicle.

Figure 13:
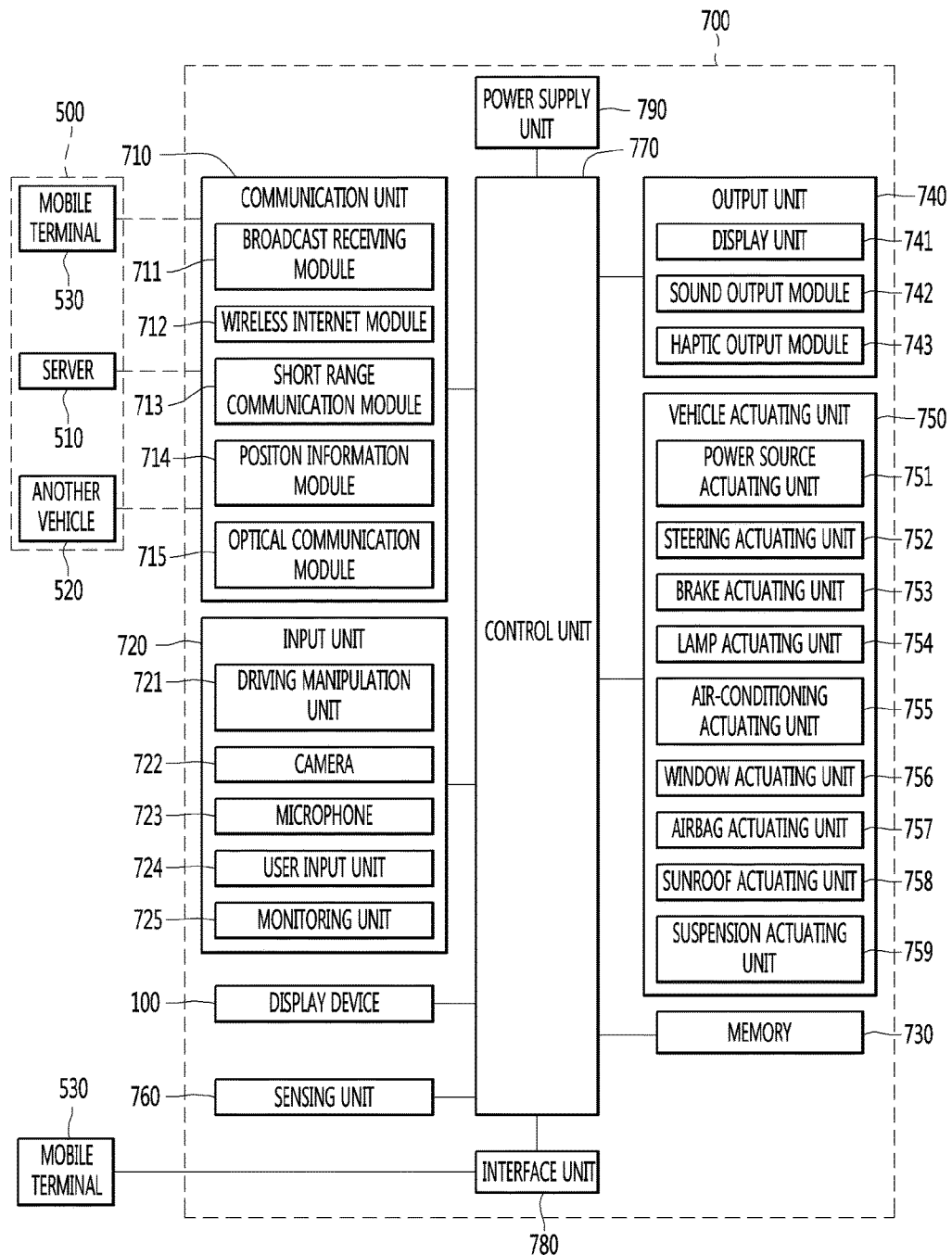
FIG. 13 is an internal block diagram of the vehicle of FIG. 12.

Referring to FIG. 13, a vehicle according to an embodiment may include a communication unit 710, an input unit 720, a sensing unit 760, an output unit 740, a vehicle actuating unit 750, a memory 730, an interface unit 780, a control unit 770, a power supply unit 790, and the display device 100.

The communication unit 710 may include one or more modules that enable wireless communication between the vehicle and the mobile terminal 530, between the vehicle and an external sever 510, or between the vehicle and another vehicle 520. Also, the communication unit 710 may include one or more modules that connect the vehicle to one or more networks.

The communication unit 710 may include a broadcast receiving module 711, a wireless internet module 712, a short-range communication module 713, a position information module 714, and an optical communication module 715. The broadcast receiving module 711 receives a broadcast signal or broadcast related information from an external broadcast management server through a broadcast channel. In this example, a broadcast includes a radio or TV broadcast.

The wireless internet module 712 indicates a module for wireless internet access and may be built into or external to the vehicle. The wireless internet module 712 is configured to transmit/receive a wireless signal in a communication network according to wireless internet technologies.

The wireless internet technology may include Wireless LAN (WLAN), Wireless-Fidelity (Wi-Fi), Wi-Fi Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), and Long Term Evolution-Advanced (LTE-A) and the wireless internet module 712 transmits/receives data according to at least one wireless internet technology including internet technologies not listed above. For example, the wireless internet module 712 may exchange data with the external server 510 wirelessly. The wireless internet module 712 may receive weather information or road traffic information (e.g., TPEG) from the external server 510.

The short-range communication module 713 may support short-range communication by using at least one of Bluetooth™, Radio Frequency Identification (RFID), Infrared Data Association (IrDA), Ultra Wideband (UWB), ZigBee, Near Field Communication (NFC), Wireless-Fidelity (Wi-Fi), Wi-Fi Direct, and Wireless Universal Serial Bus (Wireless USB) technologies.

Such a short-range communication module 713 may form a Wireless Area Network (WAN) to perform short-range communication between the vehicle and at least one external device. For example, the short-range communication module 713 may exchange data with the mobile terminal 530. The short-range module 713 may receive weather information or road traffic information (e.g., TPEG) from the mobile terminal 530. If a user gets in the vehicle, the mobile terminal 530 of the user and the vehicle may perform pairing on each other automatically or by the execution of an application by the user.

The position information module 714 is a module for acquiring the position of the vehicle and includes a GPS module as a typical example. For example, the vehicle may use a signal transmitted by a GPS satellite to acquire the position of the vehicle, when the GPS module is used.

The optical communication module 715 may include a light transmission unit and a light reception unit. The light reception unit may convert a light signal into an electrical signal to receive information. The light reception unit may include a photo diode (PD) for receiving light. The PD may convert light into an electrical signal. For example, the light reception unit may receive information on the front vehicle through light emitted from a light source that is included in the front vehicle.

The light transmission unit may include at least one light-emitting element for converting an electrical signal into a light signal. In this example, the light-emitting element may be a light-emitting diode (LED). The light transmission unit may convert an electrical signal into a light signal to transmit the light signal to the outside. For example, the light transmission unit may transmit the light signal to the outside through the on/off of the light-emitting element corresponding to a predetermined frequency. According to an embodiment, the light transmission unit may include a plurality of light-emitting element arrays. According to an embodiment, the light transmission unit may be integrated into a lamp that is installed at the vehicle. For example, the light transmission unit may be at least one of a headlight, a taillight, a stop lamp, a turn signal, and a sidelight. For example, the optical communication module 715 may exchange data with the other vehicle 520 through optical communication.

The input unit 720 may include the driving manipulation means 721, a camera 195, a microphone 723, and a user input unit 724. The driving manipulation means 721 receives a user input for driving the vehicle. (See FIG. 2 for the following description.) The driving manipulation means 721 may include the steering input means 721A, a shift input means 721D, an acceleration input means 721C, and a brake input means 721B.

The steering input means 721A receives an input for the driving direction of the vehicle from a user. The steering input means 721A may be formed in the form of a wheel so that a steering input may be performed by rotation. According to an embodiment, the steering input means 721A may also be formed as a touch screen, touch pad or button.

The shift input means 721D receives an input for the parking P, driving D, neutrality N, and rear movement R of the vehicle from the user. The shift input means 721D may be formed in the form of a lever. According to an embodiment, the shift input means 721D may also be formed as a touch screen, touch pad or button.

The acceleration input means 721D receives an n input for the acceleration of the vehicle from the user. The brake input means 721B receives an input for the speed decrease of the vehicle from the user. The acceleration input means 721C and the brake input means 721B may be formed in the form of a pedal. According to an embodiment, the acceleration input means 721C or the brake input means 721B may also be formed as a touch screen, touch pad or button.

The camera 722 may include an image sensor and an image processing module. The camera 722 may process a still image or video that is obtained by an image sensor (e.g., CMOS or CCD). The image processing module may process the still image or video acquired by the image sensor to extract necessary information and transmit the extracted information to the processor 770.

The vehicle may include the camera 722 that captures images in front of the vehicle or images around the vehicle, and the monitoring unit 725 that captures an image of the interior of the vehicle. The monitoring unit 725 may acquire an image of a passenger. The monitoring unit 725 may acquire the image of the passenger for biometrics.

Although FIG. 13 shows that the monitoring unit 725 and the camera 722 are included in the input unit, the camera 722 may also be included in the display device 100 as described above. The microphone 723 may process an external sound signal into electrical data. The processed data may be used in various methods according to a function that is executed at the vehicle.

The microphone 723 may convert a user's voice command into electrical data. The electrical data obtained through conversion may be transmitted to the control unit 770. According to an embodiment, the camera 722 or the microphone 723 may also be a component that is included in the sensing unit 760, and not in the input 720.

The user input unit 724 receives information from the user. When information is input through the user input unit 724, the control unit 770 may control the operation of the vehicle corresponding to the input information. The user input unit 724 may include a touch-type input mechanism or mechanical input mechanism. According to an embodiment, the user input unit 724 can be disposed at a region of a steering wheel. In this instance, a driver may manipulate the user input unit 724 with his or her finger, holding the steering wheel.

The sensing unit 760 senses a signal relating to the driving of the vehicle. Thus, the sensing unit 760 may include a wheel sensor, a speed sensor, a tilt sensor, a weight sensor, a heading sensor, a yaw sensor, a gyro sensor, a position module, a vehicle forward/backward movement sensor, a battery sensor, a fuel sensor, a tire sensor, a steering sensor by steering wheel rotation, a vehicle temperature sensor, a vehicle humidity sensor, an ultrasonic sensor, a radar, a Lidar, and so on.

Thus, the sensing unit 760 may acquire sensing signals for vehicle collision information, vehicle direction information, vehicle position information (GPS information), vehicle angle information, vehicle speed information, vehicle acceleration information, vehicle tilt information, vehicle forward/backward movement information, battery information, fuel information, tire information, vehicle lamp information, vehicle temperature information, vehicle humidity information, steering wheel rotation angle, and so on.

The sensing unit 760 may further include an acceleration pedal sensor, a barometric pressure sensor, an engine speed sensor, an Air Flow Sensor (AFS), an Air Temperature Sensor (ATS), a Water Temperature Sensor (WTS), a Throttle Position Sensor (TPS), a TDC sensor, a Crank Angle Sensor (CAS), and so on.

The sensing unit 760 may include a biometric recognition information sensing unit. The biometric recognition information sensing unit senses and acquires biometric recognition information on a passenger. The biometric recognition information may include fingerprint information, iris-scan information, retina-scan information, hand geometry information, facial recognition information, and voice recognition information. The biometric recognition information sensing unit may include a sensor that senses biometric recognition information of the passenger. In this instance, the monitoring unit 725 and the microphone 723 may operate as sensors. The biometric recognition information sensing unit may acquire hand geometry information and facial recognition information through the monitoring unit 725.

The output unit 740 is used for outputting information processed by the control unit 770 and may include the display unit 741, the sound output unit 742, and the haptic output unit 743. In this instance, the display unit 741 may be the display device 100 according to the above-described embodiment.

The display unit 741 may display information processed by the control unit 770. For example, the display unit 741 may display vehicle related information. In this example, the vehicle related information may include vehicle control information for direct control over the vehicle or driver assistance information for a driving guide for a driver. Also, the vehicle related information may include vehicle state information that indicates the current state of the vehicle, or vehicle operation information relating to the operation of the vehicle.

The display unit 741 may include at least one of an LCD, a TFT LCD, an OLED, a flexible display, a 3D display, and an e-ink display. The display unit 741 may form a mutual layer structure with a touch sensor or be integrally formed to implement a touch screen. The touch screen may function as the user input unit that provides an input interface between the vehicle and the user, and also provide an output interface between the vehicle and the user.

In this instance, the display unit 741 may include a touch sensor sensing a touch of the display unit 741 to be capable of receiving a control command by the touch. Accordingly, when the display unit 741 is touched, the touch sensor senses the touch, and the control unit 770 may generate, based on the touch, a control command corresponding to the touch. A thing input by the touch may be a letter, a number, or a menu item that may be instructed or designated in various modes.

The display unit 741 may include a cluster so that a driver may see vehicle state information or vehicle operation information simultaneously with driving. The cluster may be located on the dashboard. In this instance, the driver may see information displayed on the cluster, maintaining forward view.

According to an embodiment, the display unit 741 may be implemented as a HUD. When the display unit 741 is implemented as the HUD, it is possible to output information through a transparent display that is installed on the windshield. Alternatively, the display unit 741 may include a projection module to output information by using image that is projected onto the windshield.

The sound output unit 742 converts an electrical signal from the control unit 770 into an audio signal and outputs the audio signal. Thus, the sound output unit 742 may include a speaker and so on. The sound output unit 742 may also output sound corresponding to the operation of the user input unit 724.

The haptic output unit 743 generates a haptic output. For example, the haptic output unit 743 may enable a steering wheel, a safety belt and a seat to vibrate so that a user can recognize an output. The vehicle actuating unit 750 may control the operations of various apparatuses of the vehicle. The vehicle actuating unit 750 may include a power source actuating unit 751, a steering actuating unit 752, a brake actuating unit 753, a lamp actuating unit 754, an air-conditioning actuating unit 755, a window actuating unit 756, an airbag actuating unit 757, a sunroof actuating unit 758, and a suspension actuating unit 759.

The power source actuating unit 751 may perform electronic control over the power source in the vehicle. For example, when the power source is a fossil fuel based engine(not shown), the power source actuating unit 751 may perform electronic control over the engine. Thus, it is possible to control the output torque of the engine. When the power source actuating unit 751 is the engine, it is possible to restrict the output torque of the engine to restrict the speed of the vehicle.

As another example, when the power source is an electricity based motor (not shown), the power source actuating unit 751 may control the motor. Thus, it is possible to control the speed, torque and so on of the motor. The steering actuating unit 752 may perform electronic control over a steering apparatus in the vehicle. Thus, it is possible to change the driving direction of the vehicle.

The brake actuating unit 753 may perform electronic control over a brake apparatus (not shown) in the vehicle. For example, it is possible to control the operation of a brake installed at a wheel to decrease the speed of the vehicle. As another example, by enabling brakes disposed at the left wheel and the right wheel respectively to perform different operations, it is possible to adjust the driving direction of the vehicle to the left or to the right.

The lamp actuating unit 754 may control the turn on/off of lamps that are disposed inside and outside the vehicle. Also, it is possible to control the intensity, direction and so on of light emitted from the lamp. For example, it is possible to control a turn signal lamp, a brake lamp, and so on.

The air-conditioning actuating unit 755 may perform electronic control over an air conditioner (not shown) in the vehicle. For example, when the temperature inside the vehicle is high, it is possible to operate the air conditioner so that cold air is supplied into the vehicle.

The window actuating unit 756 may perform electronic control over a window apparatus in the vehicle. For example, it is possible to open or close left and right windows of the vehicle. The airbag actuating unit 757 may perform electronic control over an airbag apparatus in the vehicle. For example, it is possible to operate an airbag in a risky situation.

The sunroof actuating unit 758 may perform electronic control over a sunroof apparatus (not shown) in the vehicle. For example, it is possible to open or close the sunroof. The suspension actuating unit 759 may perform electronic control over a suspension apparatus (not shown) in the vehicle. For example, when the road surface is uneven, it is possible to control a suspension apparatus to reduce the vibration of the vehicle.

The memory 730 is electrically connected to the control unit 770. The memory 770 may store fundamental data on units, control data for operation control over the units, and input and output data. The memory 790 may be various storage devices, such as a ROM, RAM, EPROM, flash drive, and hard drive that are hardware. The memory 730 may store various pieces of data for the overall operations of the vehicle, such as programs for processing or controlling by the control unit 770.

The interface 780 may function as a path to various kinds of external devices that are connected to the vehicle. For example, the interface unit 780 may include a port connectable to the mobile terminal 530 and be connected to the mobile terminal 530 through the port. In this instance, the interface unit 780 may exchange data with the mobile terminal 530.

The interface unit 780 may function as a path through which electrical energy is supplied to the mobile terminal 530. When the mobile terminal 530 is electrically connected to the interface unit 780, the interface unit 780 supplies electrical energy supplied from the power supply unit 790 to the mobile terminal 530 according to the control of the control unit 770.

The control unit 770 may control the overall operation of each unit in the vehicle. The control unit 770 may be named an electronic control unit (ECU). Such a control unit 770 may execute a function corresponding to a transmitted signal, according to the execution signal transmission of the display device 100.

The control unit 770 may be implemented by using at least one of an ASIC, a DSP, a DSPD, a PLD, an FPGA, a processor, a controller, a micro-controller, a microprocessor, and other electrical units for executing functions. The control unit 770 may perform the role of the above-described processor 170.

That is, the processor 170 of the display device 100 may be set directly to the control unit 770 of the vehicle. In such an embodiment, it may be understood that the display device 100 refers to some components of the vehicle. Alternatively, the control unit 770 may also control components to transmit information requested by the processor 170.

The power supply unit 790 may supply power required for the operation of each component according to the control of the control unit 770. In particular, the power supply unit 770 may receive power from a battery (not shown) in the vehicle.

The display device 100 may exchange data with the control unit 770. The control unit 770 may receive navigation information from the display device 100 or a separate navigation apparatus (not shown). In this example, the navigation information may include set destination information, route information according to the destination, vehicle driving related map information, or vehicle position information.

The characteristics, structures, and effects described in the embodiments above are included in at least one embodiment but are not limited to one embodiment. Furthermore, the characteristic, structure, and effect illustrated in each embodiment may be combined or modified for other embodiments by a person skilled in the art. Thus, it would be construed that contents related to such a combination and such a variation are included in the scope of embodiments.

Embodiments are mostly described above. However, they are only examples and do not limit the inventive concept. A person skilled in the art may appreciate that many variations and applications not presented above may be implemented without departing from the essential characteristic of embodiments. For example, each component particularly represented in embodiments may be varied. In addition, it should be construed that differences related to such a variation and such an application are included in the scope of the inventive concept defined in the following claims.

A display device according to an embodiment may be applied to a display device for a vehicle navigation system, and a portable display device, such as a notebook computer, a mobile phone, or the like, as well as to a computer monitor or TV. In addition, since such a display device has advantages that it is possible to precisely sense a proximity touch and the size of bezel decreases, there is industrial applicability.

The invention claimed is:

1. A display device comprising:
   a touch window including an active area and an unactive area around the active area;
   a display unit disposed under the active area;
   a bezel frame configured to support the display unit; and
   a light sensor unit disposed on a side of the bezel frame and at an angle to a top surface of the touch window under the unactive area of the touch window and including at least one light output unit configured to output light and at least one light receiving unit configured to receive light reflected from an input tool,
   wherein the light sensor unit further comprises a lens spreading light output from the at least one light output unit or collecting light reflected from the input tool into the at least one light receiving unit,
   wherein the lens comprises:
   an external surface facing the unactive area and being parallel to the top surface of the touch window; and
   an internal surface facing the at least one light output unit and the at least one light receiving unit and having a concave shape,
   wherein at least a part of the internal surface becomes closer to the external surface as the distance from the display unit increases, and
   wherein the light sensor unit is at the angle to have a light output surface of the at least one light output unit face an upper portion of the active area.

2. The display device according to claim 1, wherein the unactive area is disposed on all sides of the active area, and
   wherein the light sensor unit is disposed under at least one side of the unactive area.

3. The display device according to claim 2, wherein the active area is a breadthwise active area that is longer in a horizontal direction than in a vertical direction and a lateral direction corresponds to the horizontal direction, and
   wherein the light sensor unit comprises a first light sensor unit disposed under a left unactive area and a second light sensor unit disposed under a right unactive area.

4. The display device according to claim 2, wherein the active area is a breadthwise active area that is longer in a horizontal direction than in a vertical direction, a lateral direction corresponds to the horizontal direction and a longitudinal direction corresponds to the vertical direction, and
   wherein the light sensor unit comprises a first light sensor unit disposed under an upper unactive area and a second light sensor unit disposed under a lower unactive area.

5. The display device according to claim 1, further comprising:
   a printed layer disposed on the unactive area and including a first hole in an area that overlaps the at least one light output unit and the at least one light receiving unit.

6. The display device according to claim 5, wherein the light sensor unit further comprises a light sensor substrate supporting the at least one light receiving unit, and a noise reducing frame disposed on the light sensor substrate.

7. The display device according to claim 6, wherein the noise reducing frame comprises a second hole in an area that overlaps the at least one light output unit and the at least one light receiving unit, and
   wherein the lens is disposed at the second hole.

8. The display device according to claim 7, wherein the noise reducing frame and the light sensor substrate form a square pillar shape and the lens covers the second hole of the noise reducing frame, and
   wherein the at least one light output unit and the at least one light receiving unit are surrounded by the noise reducing frame, the light sensor substrate and the lens.

9. The display device according to claim 8, further comprising:
   air gaps formed between the at least one light output unit and the lens and between the at least one light receiving unit and the lens.

10. The display device according to claim 6, further comprising:
    a front casing supporting the noise reducing frame and the touch window,
    wherein the front casing comprises a bumper portion disposed around the noise reducing frame.

11. The display device according to claim 1, wherein the light sensor unit further comprises a light sensor substrate supporting the at least one light output unit and the at least one light receiving unit.

12. The display device according to claim 11, wherein the bezel frame has a space under the unactive area,
    wherein the light sensor unit is disposed in the space, and
    wherein the bezel frame comprises a hole on an area that overlaps the at least one light output unit and the at least one light receiving unit.

13. The display device according to claim 12, wherein the lens is disposed at the hole of the bezel frame.

14. The display device according to claim 13, wherein the bezel frame and the light sensor substrate form a space under the unactive area, and
    wherein the at least one light output unit and the at least one light receiving unit are surrounded by the bezel frame, the light sensor substrate and the lens.

15. The display device according to claim 14, wherein the bezel frame further comprises a sidewall disposed between the light sensor unit and the display unit.

16. The display device according to claim 1, wherein light that the at least one light output unit outputs is infrared light.

17. A vehicle comprising the display device according to claim 1.

18. The vehicle according to claim 1, wherein the unactive area is disposed on all sides of the active area.

* * * * *